(12) United States Patent
Song et al.

(10) Patent No.: US 9,164,105 B2
(45) Date of Patent: Oct. 20, 2015

(54) PANCREATIC CANCER BIOMARKER USING THE CHARACTERISTICS OF PANCREATIC CANCER STEM CELLS, AND USE THEREOF

(75) Inventors: Si Young Song, Seoul (KR); Soo Been Park, Seoul (KR); Sun A Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 13/979,615

(22) PCT Filed: Jan. 13, 2012

(86) PCT No.: PCT/KR2012/000338
§ 371 (c)(1),
(2), (4) Date: Aug. 28, 2013

(87) PCT Pub. No.: WO2012/096545
PCT Pub. Date: Jul. 19, 2012

(65) Prior Publication Data
US 2014/0039033 A1 Feb. 6, 2014

(51) Int. Cl.
*A61K 38/00* (2006.01)
*G01N 33/68* (2006.01)
*G01N 33/574* (2006.01)
*C12Q 1/68* (2006.01)
*C12N 15/113* (2010.01)

(52) U.S. Cl.
CPC .......... *G01N 33/6893* (2013.01); *C12N 15/113* (2013.01); *C12Q 1/6881* (2013.01); *C12Q 1/6886* (2013.01); *G01N 33/57438* (2013.01); *C12N 2310/14* (2013.01); *C12N 2310/531* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2006/0019256 A1 1/2006 Clarke et al.

OTHER PUBLICATIONS

Cha et al (Cancer Epidemiology, 2009, 33:281-287).*
Qu et al (Journal of Clinical Investigation, Jan. 2011, 121:212-225; published online Dec. 1, 2010).*
International Search Report for PCT/KR2012/000338, Dec. 3, 2012.
Mee-Kyung Cha et al. Peferential overexpression of glutaredoxin3 in human colon and lung carcinoma. Cancer Epidemiology. 2009, vol. 33, No. 3/4, pp. 281-287.
Laura C. Hautala et al. Glycodelin reduces breast cancer xenograft growth in vivo. International Journal of Cancer. 2008, vol. 123, Issue 10, pp. 2279-2284.
Haijing Zhang et al. Profiling the potential biomarkers for cell differentiation of pancreatic cancer using iTRAQ and 2-D LC-MS/MS. Proteomics Clin. Appl. 2009, vol. 3, pp. 862-871.

\* cited by examiner

*Primary Examiner* — Laura B Goddard
(74) *Attorney, Agent, or Firm* — The PL Law Group, PLLC

(57) ABSTRACT

The present invention relates to a novel molecular marker for pancreatic cancer stem cells and pancreatic cancer, to a marker detection method, and to a screening method. The present invention is a marker discovered from the cell lines of pancreatic cancer, wherein the marker may detect pancreatic cancer, in particular early pancreatic cancer, through the detection of a pancreatic cancer stem cell marker. In addition, the marker of the present invention may enable an accurate diagnosis and prognosis analysis of pancreatic cancer.

1 Claim, 27 Drawing Sheets

Fig. 5a
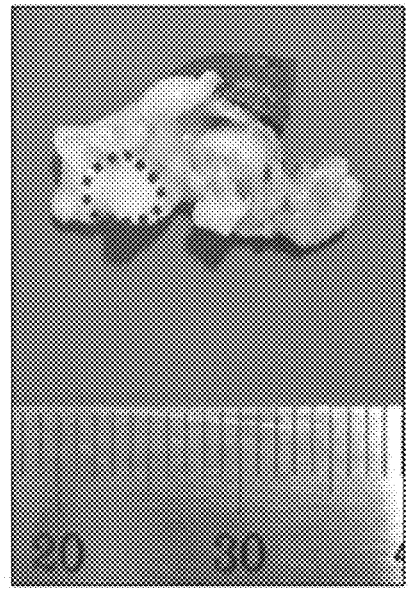
Hpac
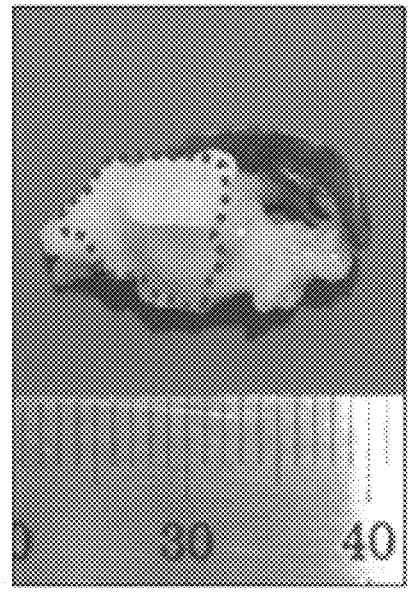
Hpac-sphere
Lung metastasis

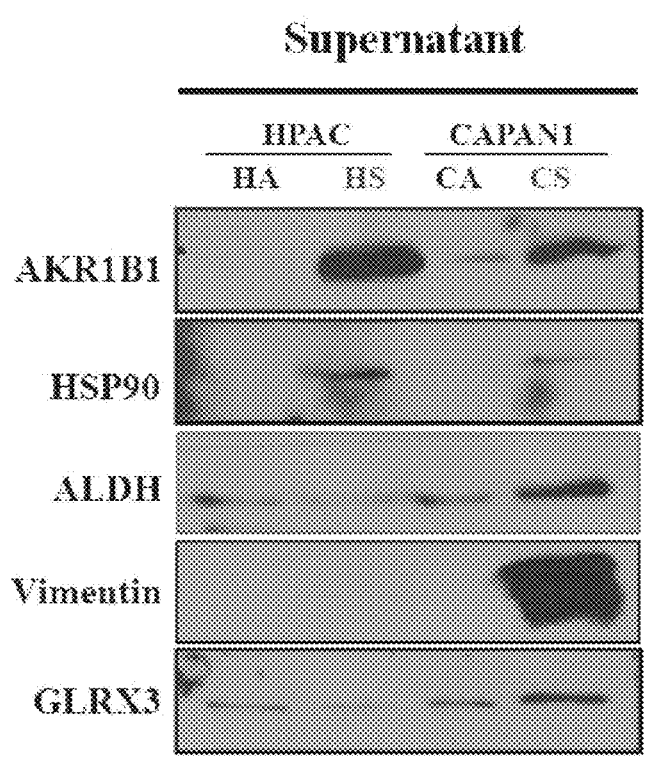

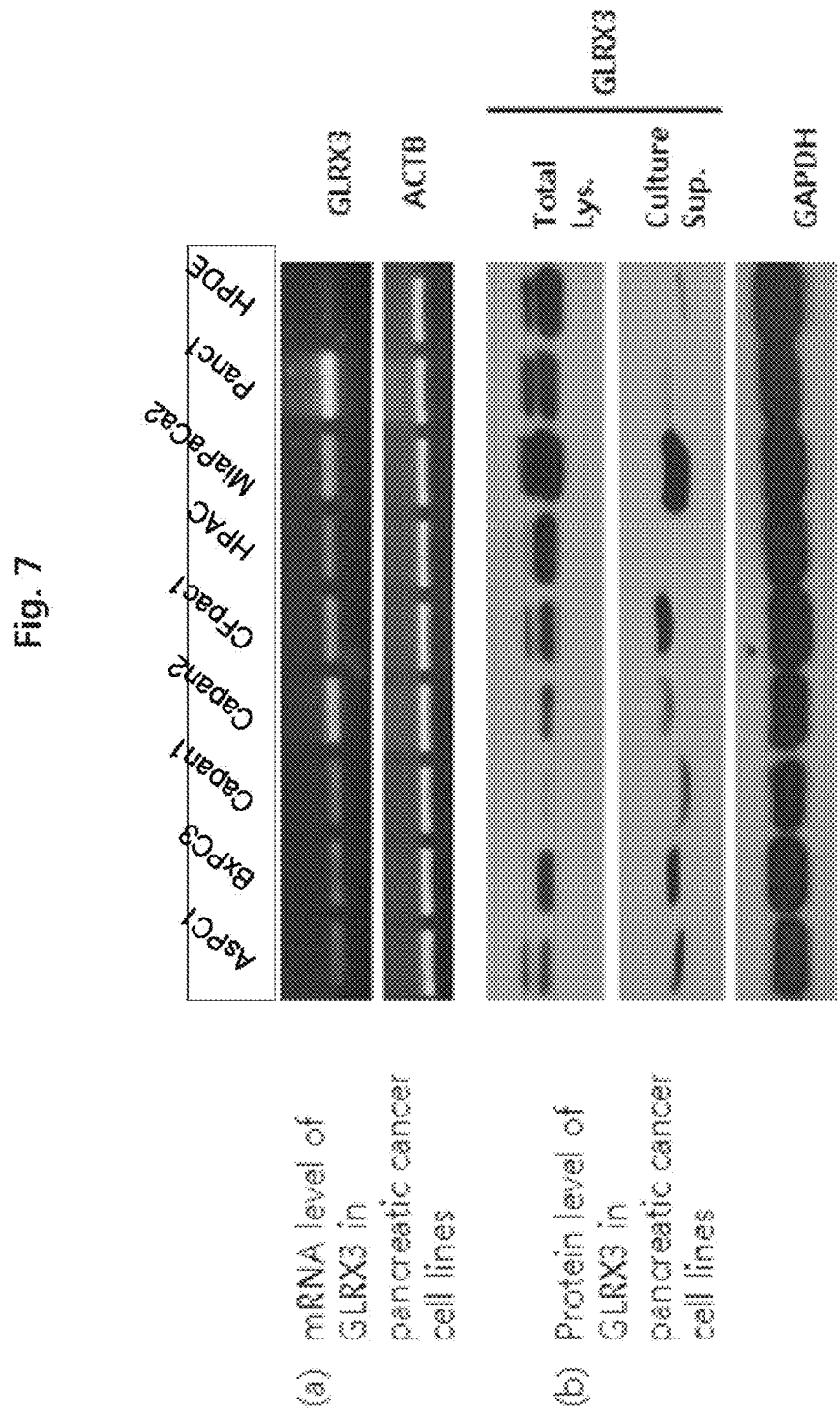

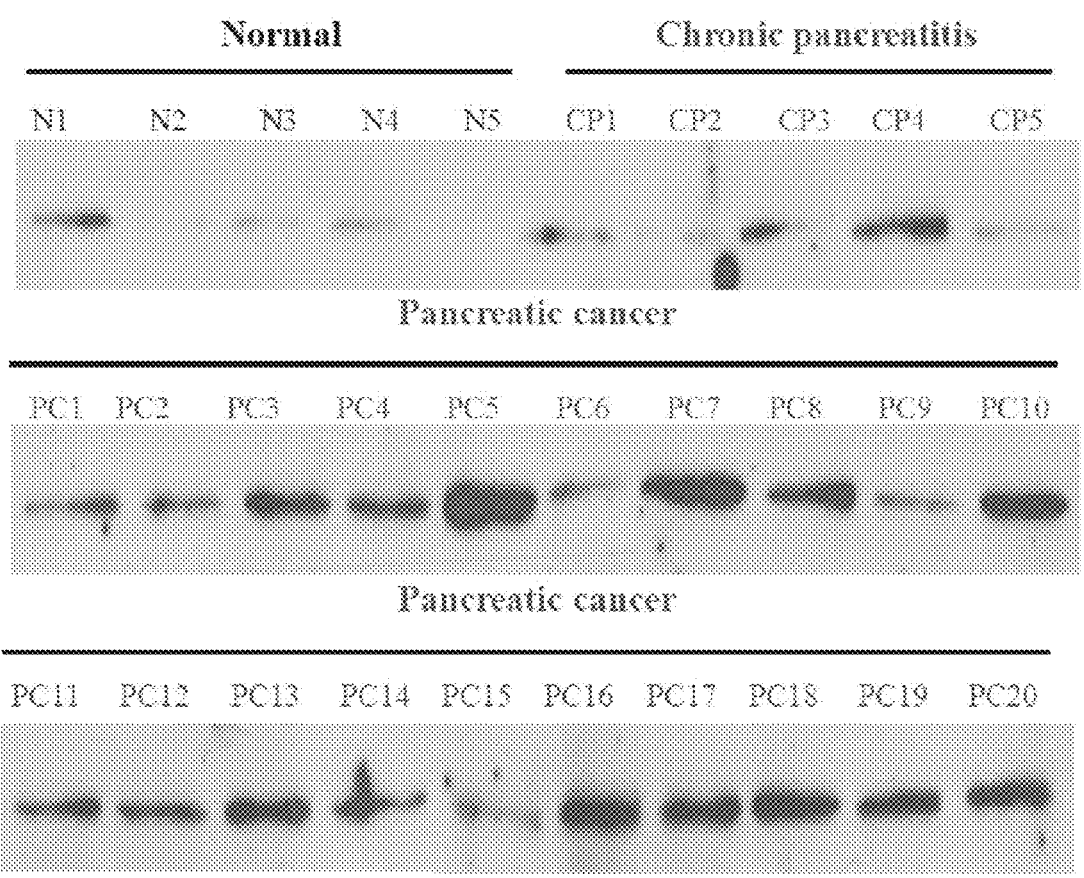

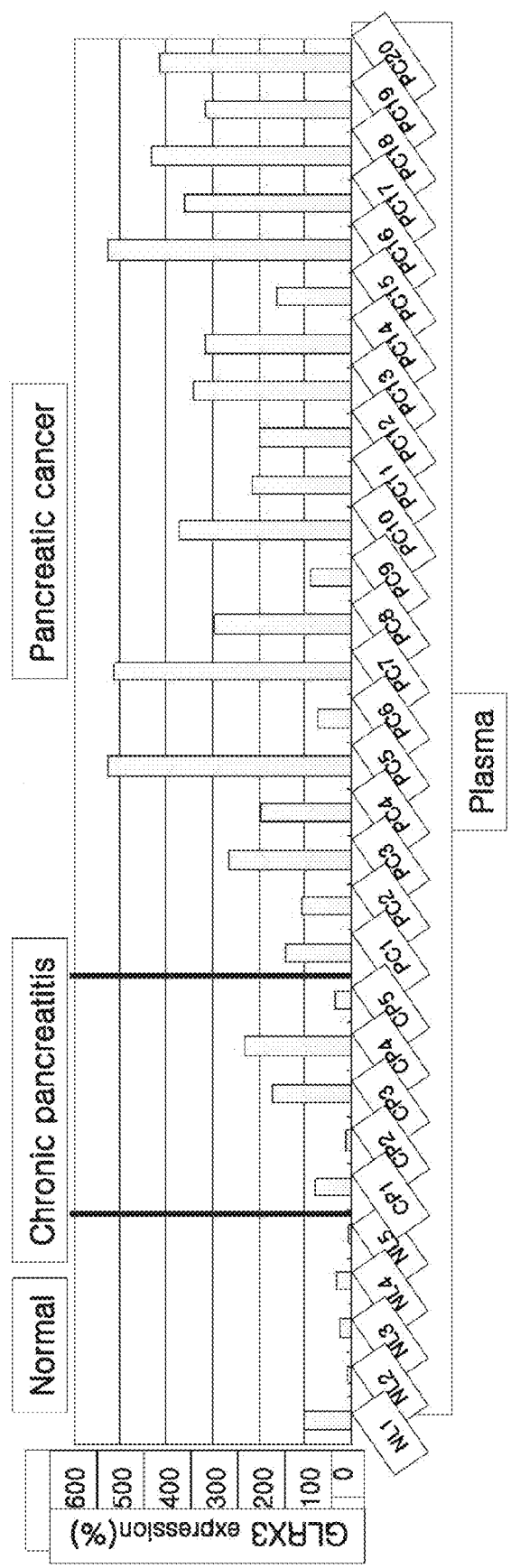

PANCREATIC CANCER BIOMARKER USING THE CHARACTERISTICS OF PANCREATIC CANCER STEM CELLS, AND USE THEREOF

CROSS REFERENCE TO RELATED APPLICATIONS AND CLAIM OF PRIORITY

This patent application is a National Phase application under 35 U.S.C. §371 of International Application No. PCT/KR2012/000338, filed Jan. 13, 2012, which claims priority to Korean Patent Application No. 10-2011-0003423 filed Jan. 13, 2011, entire contents of which are incorporated herein by reference.

FIELD OF THE INVENTION

The present invention relates to a pancreatic cancer stem cell-specific novel biomarker for and use thereof.

DESCRIPTION OF THE RELATED ART

Cancer stem cells are cancer cells that possess the abilities to maintain and regenerate cancer tissues like normal stem cells. Cancer stem cells are not only thought to be involved in oncogenesis, but also have been reported that they profoundly influence cancer recurrence, metastasis or resistance to chemotherapy by involving regeneration of cancer cells after anticancer therapies (BB Zhou et al. Nature Reviews Drug Discovery, 8:806-823 (2009)). Therefore, for diagnosing and treating cancer fundamentally, it should be focused on cancer stem cells which play a pivotal rule in occurrence, maintenance and recurrence with a rare population in cancer tissue. A better understanding of cancer stem cells would be helpful to develop diagnostic markers for the early diagnosis.

Pancreatic cancer is one of the most deadly human tumors with 1-4% of 5 year survival rate and 5 months of median survival time, and it has an extremely poor prognosis. Since 80-90% of patients are diagnosed at an advanced stage of being not possible to cure by curative resection, it leads to a poor clinical outcome. In addition, anticancer therapies mainly depend on chemotherapies. Therefore, development for the early diagnosis method in pancreatic cancer is urgently needed than any other human cancers.

To date, therapeutic effects of several anticancer agents including 5-fluorouracil, gemcitabine and tarceva known to be effective in pancreatic cancer are very disappointing, and there is only approximately 15% of the response rate to chemotherapy. These facts suggest that developments for the early diagnosis method and therapeutic method to pancreatic cancer in more effective manner are urgently needed.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have made intensive studies to develop a novel diagnosable biomarker for pancreatic cancer stem cell and/or pancreatic cancer in more accurate and rapid manner. As results, they have found that the developed biomarkers based on biological characteristics of pancreatic cancer stem cells may be used as markers for diagnosing pancreatic cancer in its early stage and predicting its prognosis, and targets for treating pancreatic cancer.

Accordingly, it is an object of this invention to provide a kit for detecting a pancreatic cancer stem cell-specific biomarker.

It is another object of this invention to provide a kit for diagnosing pancreatic cancer or for analyzing pancreatic cancer prognosis.

It is still another object of this invention to provide a method for detecting a pancreatic cancer stem cell marker to provide information for diagnosing pancreatic cancer or for analyzing pancreatic cancer prognosis.

It is further object of this invention to provide a method for detecting a pancreatic cancer marker to provide information for diagnosing pancreatic cancer or for analyzing pancreatic cancer prognosis.

It is still further object of this invention to provide a method for screening a therapeutic substance for preventing or treating pancreatic cancer.

It is further object of this invention to provide a pharmaceutical composition for preventing or treating cancer.

It is still further object of this invention to provide a method for inhibiting proliferation of a cancer cell.

It is further object of this invention to provide a method for preventing or treating cancer.

Other objects and advantages of the present invention will become apparent from the following detailed description together with the appended claims and drawings.

In one aspect of this invention, there is provided a kit for detecting a pancreatic cancer stem cell marker comprising:

(i) an oligopeptide, a monoclonal antibody, a polyclonal antibody, a chimeric antibody, a ligand, a PNA (Peptide nucleic acid) or an aptamer specifically binding to at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP_653280.1, GenBank accession No. BAF83085.1, GenBank accession No. AAH70129.1, GenBank accession No. 1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1; or (ii) a primer or a probe specifically hybridized with the polynucleotide encoding each of the proteins.

In another aspect of this invention, there is provided a kit for diagnosing pancreatic cancer or for analyzing pancreatic cancer prognosis comprising:

(i) an oligopeptide, a monoclonal antibody, a polyclonal antibody, a chimeric antibody, a ligand, a PNA (Peptide nucleic acid) or an aptamer specifically binding to at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP 653280.1, GenBank accession No. BAF83085.1, GenBank accession No. AAH70129.1, GenBank accession No. 1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1; or (ii) a primer or a probe specifically hybridized with the polynucleotide encoding each of the proteins.

The present inventors have made intensive studies to develop a novel diagnosable biomarker for pancreatic cancer stem cell and/or pancreatic cancer in more accurate and rapid manner. As results, they have found that the developed biomarkers based on biological characteristics of pancreatic cancer stem cells may be used as markers for diagnosing pancreatic cancer in its early stage and predicting its prognosis, and targets for treating pancreatic cancer.

The present invention is a novel pancreatic cancer stem cell marker developed by identifying proteins specifically expressed in pancreatic cancer stem cells separated from pancreatic cancer cell lines, and it may be diagnosis pancreatic cancer in its early stage with great accuracy and analyze prognosis.

The expression "kit for diagnosing pancreatic cancer or for analyzing pancreatic cancer prognosis" as used herein refers to a kit including a composition for diagnosing pancreatic cancer or for analyzing pancreatic cancer prognosis. Therefore, there is no intended distinction between the expression "kit for diagnosing pancreatic cancer or for analyzing pancreatic cancer prognosis" and the expression "composition for diagnosing pancreatic cancer or for analyzing pancreatic cancer prognosis", and these terms will be used interchangeably.

The term "diagnosis" as used herein includes the following matters to determine susceptibility of a subject to a particular disease or disorder; to evaluate whether a subject has a particular disease or disorder; to assess a prognosis of a subject suffering from a specific disease or disorder (e.g., identification of pre-metastatic or metastatic cancer conditions, determination of cancer stage, or investigation of cancer response to treatment); or therametrics (e.g., monitoring conditions of a subject to provide an information to treatment efficacy).

The term "pancreatic cancer" as used herein refers to cancer which is derived from pancreatic cells. Although there are several different types of pancreatic cancers, pancreatic adenocarcinoma accounts for approximately 90% of them such that pancreatic cancer commonly used means pancreatic adenocarcinoma. Approximately 5-10% of pancreatic cancer patients have a genetic predisposition. In pancreatic cancer patients with family history of pancreatic cancer, the incidence of pancreatic cancer (approximately 7.8%) is higher than that of normal (0.6%). pancreatic cancer is one of the rarely curable human diseases, with a 5-year survival rate of less than 5%. Since pancreatic cancer is found at an advanced stage, less than 20% of patients may be possible to cure by curative resection. In addition, micrometastasis occurs even though pancreatic cancer is completely removed with the naked eye. Moreover, it has resistances to chemotherapy and radiotherapy. Therefore, the most important way to improve the survival rate is curative resection by detecting in an early stage.

The present inventors have found that the present marker may be used as markers for detecting onset of pancreatic cancer from the object with high sensitivity and reliability.

The term "diagnostic marker", "marker for diagnosing" or "diagnosis marker" as used herein refers to a substance capable of being used to distinguish pancreatic cancer cells from normal cells and diagnose pancreatic cancer and includes organic biomolecules of which quantities are increased in the pancreatic cancer cells or tissues as compared to the normal cells, such as polypeptides or nucleic acids (for example, mRNA), lipids, glycollipids, glycoproteins, sugars (monosaccharide, disaccharide, oligosaccharide, etc.), or the like.

With respect to the objects of the present invention, the pancreatic cancer diagnosis marker may be at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP_653280.1, GenBank accession No. BAF83085.1, GenBank accession No. AAH70129.1, GenBank accession No. 1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1, and its expression is increased in pancreatic cancer stem cells.

These markers include DNA or mRNA encoding any one of proteins as well as proteins, and preferably combination containing two or more markers.

The term used herein "measurement of the protein expression level" in conjunction with pancreatic cancer diagnosis means a process of confirming whether or not the protein expressed from the pancreatic cancer marker genes is present in a biological sample and an expression degree thereof in order to diagnose pancreatic cancer. Preferably, an amount of proteins may be confirmed using the antibody specifically binding to the protein of the gene. Analysis methods for measuring protein levels include a western blotting method, an enzyme linked immunosorbent assay (ELISA) method, a radioimmunoassay (RIA) method, a radioimmunodiffusion method, an ouchterlony immunodiffusion method, a rocket immunoelectrophoresis method, an immunohistostaining method, an immunoprecipitation assay method, a complement fixation assay method, a fluorescence activated cell sorter (FACS) method, a protein chip assay method, or the like, but is not limited thereto.

The term used herein "antibody" means a specific protein molecule that indicates an antigenic region. With respect to the objects of the present invention, the antibody specifically binds to a marker protein and includes all of the polyclonal antibodies, monoclonal antibodies, and recombinant antibodies.

As described above, since the novel pancreatic cancer marker proteins are identified, antibody production using the pancreatic cancer marker proteins may be easily carried out using techniques widely known in the art.

The polyclonal antibody may be produced by a method widely known in the art, which includes a method of injecting the pancreatic cancer marker protein antigen into an animal and collecting blood samples from the animal to obtain serum containing antibodies. This polyclonal antibody may be prepared from a certain animal host, such as goats, rabbits, sheep, monkeys, horses, pigs, cows, and dogs.

The monoclonal antibody may be prepared by a method widely known in the art, such as a hybridoma method (1976) (Kohler and Milstein, *European Journal of Immunology* 6: 511-519), or a phage antibody library technique (Clackson et al., *Nature,* 352:624-628, 1991; Marks et al., *J. Mol. Biol.,* 222:58, 1-597, 1991). The antibody prepared by the above methods may be isolated and purified using methods such as gel electrophoresis, dialysis, salting out, ion exchange chromatography, affinity chromatography, and the like.

In addition, the antibody of the present invention may include functional fragments of antibody molecules as well as complete forms thereof having two full-length light chains and two full-length heavy chains. The functional fragments of antibody molecules refer to fragments retaining at least antigen-binding function, and include Fab, F(ab'), F(ab')2, Fv, and the like In the present invention, the aptamers include oligo nucleic acid or peptide molecules, of which details can be found in Bock L C et al., *Nature* 355 (6360):564-6 (1992); Hoppe-Seyler F, Butz K "Peptide aptamers: powerful new tools for molecular medicine". *J Mol. Med.* 78(8):426-30 (2000); Cohen B A, Colas P, Brent R. "An artificial cell-cycle inhibitor isolated from a combinatorial library". *Proc Natl Acad Sci USA.* 95(24):14272-7 (1998).

According to an embodiment, the present invention includes an oligopeptide, a monoclonal antibody, a polyclonal antibody, a chimeric antibody, a ligand, a PNA (Peptide nucleic acid) or an aptamer specifically binding to at least one protein selected from the group consisting of the proteins described above to diagnosis pancreatic cancer stem cell and/or pancreatic cancer, more preferably oligopeptide, a monoclonal antibody, a polyclonal antibody or a chimeric antibody, still more preferably a monoclonal antibody or a polyclonal antibody, and most preferably a monoclonal antibody.

In the present invention, the antibody is preferably a micro particle-conjugated antibody. The micro particle may be preferably colored latex or colloidal gold particle. In the present invention, any antibody may be used as long as it can be applied to the quantitative analysis of the expression level of the proteins encoded by known mRNA gene to the 20 markers as described above. Preferable is an antibody used in an immunoassay kit, and most preferably a Luminex assay kit, a protein microarray kit or an ELISA kit.

The Luminex assay kit, the protein microarray kit and the ELISA kit include a poly- and monoclonal antibody to at least one protein selected from the group consisting of the proteins described above, and a label-conjugated secondary antibody to the poly- or monoclonal antibody.

The present kit includes an immunochromatographic strip kit, a Luminex assay kit, a protein microarray kit, an ELISA kit or an immunodot kit, but is not limited thereto.

The kit may further include essential elements required for performing ELISA. The ELISA kit includes antibodies specific to marker proteins. The antibodies may be monoclonal, polyclonal or recombinant antibodies, which have high specificity and affinity to each marker protein and have little cross-reactivity to other proteins. In addition, the ELISA kit may include an antibody specific to a control protein. The ELISA kit may further include reagents capable of detecting bound antibodies, for example, a labeled secondary antibody, chromophores, enzymes (e.g., conjugated with an antibody) and their substrates or other substances capable of binding to the antibodies.

In addition, the kit may further include essential elements required for performing the protein microarray for analyzing combined markers simultaneously. The microarray kit includes antibodies specific to marker proteins bound to a solid support. The antibodies may be monoclonal, polyclonal or recombinant antibodies, which have high specificity and affinity to each marker protein and have little cross-reactivity to other proteins. In addition, the protein microarray kit may include an antibody specific to a control protein. The protein microarray kit may further include reagents capable of detecting bound antibodies, for example, a labeled secondary antibody, chromophores, enzymes (e.g., conjugated with an antibody) and their substrates or other substances capable of binding to the antibodies.

The method for analyzing sample using the protein microarray is as follows: isolating protein from sample; hybridizing the isolated protein with protein chip to form antigen-antibody complexes; and verifying protein presences or levels to provide information required for diagnosing pancreatic cancer.

The luminex assay is high-throughput quantification method which can analyze as many as 100 analytes at the same time even if the patient samples are present in a small amount (10-20 μL) and are not pretreated. The luminex assay is highly sensitive (pg level) and can perform quantitative analysis within a short time (3-4 hours), so that it is used as an alternative to ELISA or ELISPOT assay. The luminex assay is a multiplexed fluorescent microplate method by which 100 or more biological samples can be analyzed in each well of 96-well plates and employs two laser detectors to progress signal transmission in real time, so that polystyrene beads can be discriminated by 100 or more colors. 100 beads are designed in the following manner. Red fluorescent beads and orange fluorescent beads are divided into 10 or more classes according to intensities on respective sides. Within the matrix, the columns contain beads at different ratios of red and orange colors to form 100 color-coded bead set in total. Also, each bead is coated with an antibody to a target protein and thus can be used for protein quantification through immune responses. In this assay, a sample is analyzed using two laser rays. One laser is used to detect beads to identify the inherent bead number provided while the other laser functions to sense a sample protein reacted with the antibody conjugated to the bead. Therefore, 100 different proteins can be analyzed at the same time in one well. This assay also enjoys the advantage of sensing a sample even if it is present in an amount of as small as 15 μL.

A luminex kit with which a luminex assay can be performed in accordance with the present invention includes an antibody specific to the marker protein. The antibody may be a monoclonal, polyclonal or recombinant antibody, which has high specificity and affinity to each marker protein and rarely has cross-reactivity to other proteins. In addition, the luminex kit may include an antibody specific for a control protein. The luminex kit may further include reagents capable of detecting bound antibodies, for example, a labeled secondary antibody, chromophores, enzymes (e.g., conjugated with an antibody) and their substrates or other substances capable of binding to the antibodies. The antibody may be a micro particle-conjugated antibody. The micro particle may be colored latex or colloidal gold particle.

In the present kit, the diagnostic kit for pancreatic cancer including an immunochromatographic strip for diagnosing pancreatic cancer is characterized by including essential elements required for performing a rapid test which gives an analysis result within 5 min. Preferably, the immunochromatographic strip includes (a) sample pad; (b) conjugate pad; (c) test membrane treated with test line and control line (d) absorption pad; and (e) support. In addition, the rapid test kit with an immunochromatographic strip includes antibodies specific to marker proteins. The antibodies may be monoclonal, polyclonal or recombinant antibodies, which have high specificity and affinity to each marker protein and rarely have cross-reactivity to other proteins. In addition, the rapid test kit may include an antibody specific for a control protein. The rapid test kit may further include other substances necessary for the diagnosis, for example, a membrane on which specific antibodies and secondary antibodies are immobilized, a membrane with antibody-conjugated beads bound thereto, an absorbent pad, and a sample pad.

In the present invention, the measurement of protein levels by immunodot assay may be carried out by (a) dotting a biological sample on a membrane; (b) reacting the sample with antibodies specific for the proteins encoded by one or more genes selected from a group consisting of the 20 genes; and (c) adding a labeled secondary antibody to the membrane and developing a color. The ELISA assay is preferably a sandwich ELISA assay which can be implemented by (a) immobilizing Antibody 1 to the proteins of one or more genes selected from a group consisting of nucleotide sequences to the 20 markers; (b) reacting the immobilized Antibody 1 with a biological sample from a patient with suspected pancreatic cancer to form an antigen-antibody complex; (c) binding to the complex labeled Antibody 2 specific for the proteins encoded by one or more genes selected from a group consisting of nucleotide sequences to the 20 markers; and (d) detecting the label to determine the protein level. The protein microarray assay preferably comprises (a) immobilizing onto a chip a polyclonal antibody specific for the proteins encoded by one or more genes selected from a group consisting of nucleotide sequences to the 20 markers; (b) reacting the immobilized Antibody 1 with a biological sample from a patient with suspected pancreatic cancer to form an antigen-antibody complex; (c) binding to the complex a labeled monoclonal antibody specific for the proteins encoded by one or more genes selected from a group consisting of nucleotide sequences to the 20 markers; and (d) detecting the label to determine the protein level.

Through the analysis assays, a quantitative comparison can be made between the antigen-antibody complexes in a normal control and a patient with suspected pancreatic cancer. Based on this comparison, a significant increase in the level of the pancreatic cancer marker gene can be determined, therefore, giving information necessary for the diagnosis of pancreatic cancer.

As used herein, the term "antigen-antibody complex" is intended to refer to binding products of a pancreatic cancer marker protein to an antibody specific thereto. The antigen-antibody complex formed may be quantitatively determined by measuring the signal intensity of a detection label.

This detection label may be selected from a group consisting of enzymes, fluorescent substances, ligands, luminescent substances, microparticles, redox molecules, and radioactive isotopes, but is not necessarily limited thereto. In the case in which enzymes are used as the detecting label, examples of available enzymes include β-glucuronidase, β-D-glucosidase, β-D-galactosidase, erase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase, and the like, but are not limited thereto. Examples of the fluorescent substances include fluorescin, isothiocyanate, rhodamine, phycoerythrin, phycocyanin, allophycocyanin, o-phthaldehyde, fluorescamin, and the like, but not limited thereto. Examples of the ligands include biotin derivatives, and the like, but are not limited to, biotin derivatives. Examples of luminescent substances include acridinium esters, luciferin, luciferase, and the like, but are not limited thereto. Examples of the micro-particles include colloidal gold, colored latex, and the like, but are not limited thereto. Examples of the redox molecules include ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, $[MO(CN)_8]^{4-}$, and the like, but are not limited thereto. Examples of the radioactive isotopes include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, and the like, but are not limited thereto.

Preferably, the protein expression levels may be measured by the ELISA method. Examples of the ELISA method include various ELISA methods such as a direct ELISA method using a labeled antibody recognizing an antigen attached to a solid support, an indirect ELISA using a labeled antibody recognizing a capture antibody in the antigen complexes recognizing an antigen attached to a solid support, a direct sandwich ELISA method using another labeled antibody recognizing an antigen in an antigen-antibody complex attached to a solid support, and an indirect sandwich ELISA, in which another labeled antibody recognizing an antigen in an antigen-antibody complex attached to a solid support is reacted, and then a secondary labeled antibody recognizing the another labeled antibody is used. More preferably, the protein expression levels may be detected by the sandwich ELISA method, where a sample reacts with an antibody attached to a solid support, and the resulting antigen-antibody complexes are detected by adding a labeled antibody specific to the antigen, followed by enzymatic development, or by first adding an antigen-specific antibody and then a secondary labeled antibody which binds to the antigen-specific antibody, followed by enzymatic development. The existence of pancreatic cancer may be diagnosed by measuring the formation degree of complex of the pancreatic cancer marker protein and the antibody.

Further, the protein expression levels are preferably measured by western blotting using at least one antibody to the pancreatic cancer marker. Total proteins are isolated from the sample, electrophoresed to be separated according to sizes, transferred onto a polyvinylidene fluoride membrane, and reacted with an antibody. The amount of proteins produced by gene expression is determined by measuring the amount of produced antigen-antibody complexes using a labeled antibody, thereby diagnosing the incidence of pancreatic cancer. The detection method is performed by assessing expression levels of marker genes in the control and the cells in which pancreatic cancer occurs. mRNA or protein levels may be expressed as an absolute (e.g., µg/ml) or relative (e.g., relative intensity of signals) difference in the amount of marker proteins.

In addition, the protein expression levels are preferably measured by immunohistostaining using at least one antibody to the pancreatic cancer marker. Normal pancreatic epithelial tissue and cancer suspected tissue were collected and fixed, and then paraffin-embedded blocks were prepared according to a widely known method. The blocks were cut into small sections having a thickness of several um and attached to glass slides, and then were reacted with one selected from the above antibodies according to a known method. Subsequently, the unreacted antibodies were washed, and the reacted antibodies were labeled with one selected from the above mentioned detection labels and then observed under a microscope.

In addition, the protein expression levels are preferably measured using a protein chip in which at least one antibody to the pancreatic cancer marker is arranged at a predetermined position and fixed at high density. According to the method of analyzing the sample using the protein chip, proteins are isolated from the sample, the isolated proteins are mixed with the protein chip to form antigen-antibody complexes, the formed complexes are read, and presence or expression degrees of the protein is confirmed, such that incidence of the pancreatic cancer may be diagnosed.

In the present invention, the term "biological sample" refers to tissue, cells, whole blood, serum, plasma, saliva, sputum, cerebrospinal fluid, or urine, and most preferably serum.

The term "measurement of polynucleotide" or corresponding phrases, as used herein, are intended to refer to a process of assessing the presence and expression levels of polynucleotide encoding the present protein marker in biological samples for diagnosing pancreatic cancer, in which the amount of polynucleotide is measured. Analysis methods for measuring polynucleotide levels include, but are not limited to, RT-PCR, competitive RT-PCR, real-time RT-PCR, RNase protection assay (RPA), Northern blotting and DNA chip assay.

The nucleotide sequence encoding the present protein marker selected from the group consisting of proteins describe above may include its homologous sequences.

Preferably, the present polynucleotide means a fragment of DNA or mRNA.

The probe or primer used in the present kit for diagnosing has a polynucleotide sequence encoding each of the proteins and a complementary sequence to the polynucleotide sequence.

In the present invention, the term "primer" means a short nucleic acid sequence having the free 3'-OH group, which forms a base-pair with a complementary template and serves as a starting point for template strand replication.

The primer may initiate DNA synthesis in the presence of four different nucleoside triphosphates and an agent for polymerization (i.e, DNA polymerase or reverse transcriptase) in an appropriate buffer and at a suitable temperature. The primer of the present invention, which is a primer specific to each of the marker genes, may be sense and anti-sense nucleic acids having sequences of 7 to 50 nucleotides. In addition, the primer of the present invention may be used as additional features as well as the basic properties of the primer acting as the starting point of DNA synthesis are not changed.

The primer of the present invention may be chemically synthesized by a phosphoramidite solid support method or other well-known methods. This nucleic acid sequence may also be deformed by the known methods in the art. Nonrestrictive examples of this deformation may include methylation, capping, substitution to analogues of at least one natural nucleotide, and deformation between nucleotides, for example, deformation into an uncharged connector (for example, methyl phosphonate, phosphotriester, phosphoramidate, carbamate, or the like) or a charged connector (for example, phosphorothioate, phosphorodithioate, or the like). The nucleic acid may contain at least one additional covalently bonded residue, for example, proteins (for example, nuclease, toxin, antibody, signal peptide, poly-L-lysine, or the like), an insert material (acridine, psoralene, or the like), a chelating agent (for example, a metal, a radioactive metal, iron, an oxidative metal, or the like), and alkylating agent. The nucleic acid sequence of the present invention may also deformed using a marker capable of directly or indirectly providing a detectable signal. Examples of the marker include a radioactive isotope, a fluorescent molecule, biotin, and the like.

As used herein, the term "probe" means a natural or modified monomer, or a linear oligomer having linkages, wherein the natural or modified monomer includes deoxyribonucleotides and ribonucleotides that can be hybridized with a specific nucleotide sequence. Preferably, the present probe is a single-strand form, and oligodeoxyribonucleotide.

Where probes are used, they are hybridized with cDNA molecules. in the present invention, suitable hybridization conditions may be routinely determined by optimization procedures. To establish a protocol for use of laboratory, these procedures may be carried out by various methods known to those ordinarily skilled in the art. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

In still another aspect of this invention, there is provided a method for detecting a pancreatic cancer stem cell comprising, detecting in a human biological sample at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP_653280.1, GenBank accession No. BAF83085.1, GenBank accession No. AAH70129.1, GenBank accession No. 1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1; or the polynucleotide encoding each of the proteins.

In further aspect of this invention, there is provided a method for diagnosing pancreatic cancer comprising, detecting in a human biological sample at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP 653280.1, GenBank accession No. BAF83085.1, GenBank accession No. AAH70129.1, GenBank accession No.

1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1; or the polynucleotide encoding each of the proteins.

Analysis methods for measuring level of the protein selected from the group consisting of the proteins described above or the polynucleotide encoding each of the proteins may use methods known in the art, and include, but are not limited to, RT-PCR, competitive RT-PCR, real-time RT-PCR, RNase protection assay (RPA), Northern blotting and DNA chip assay.

The present method for detecting pancreatic cancer diagnostic marker is performed as follows: measuring expression levels of the protein selected from a group consisting of the proteins or the polynucleotide encoding each of the proteins in human pancreatic cell sample; and comparing the measured expression levels with those of protein and nucleotide of the normal control.

Where the present method for detecting pancreatic cancer diagnostic marker is performed in cell sample of pancreatic cancer patient, prognosis of the patient may be determined.

The normal control sample refers to pancreatic cells collected from human which has never cancer, normal pancreatic cells without cancer, and samples which has been already confirmed that has never cancer stem cells. For example, there are pancreatic cancer cell line samples confirmed that spheres are not formed under non-adhesive culture conditions, or cell samples determined to non-malignant other than cancer of pancreatic cancer patient, but not limited thereto. The expression level of at least one protein selected from the group consisting of the proteins described above or the polynucleotide encoding each of the proteins in the normal control sample may be measured using the same method as described above.

By the detection methods, the expression level of at least one protein selected from the group consisting of the proteins described above or the polynucleotide encoding each of the proteins in pancreatic cancer patient may be compared with that in the normal control, and the presence of cancer stem cells in pancreatic cancer patient sample may be evaluated by determining significant difference between them.

Specifically, where the expression level of at least one protein selected from the group consisting of the proteins described above or the polynucleotide encoding each of the proteins in pancreatic cancer patient sample is more than 150% of that in normal control sample, it is determined that pancreatic cancer stem cells exist.

In still further aspect of this invention, there is provided a method for screening a therapeutic substance for preventing or treating pancreatic cancer comprising:

(a) contacting a test substance of interest for analysis to a cell or a tissue containing at least one protein selected from the group consisting of the proteins of GenBank accession number AAH14372.2, GenBank accession No. CAD89908.1, GenBank accession No. NP_001077415.1, GenBank accession No. CAI21475.1, GenBank accession No. NP_653337.1, GenBank accession No. CAA27309.1, GenBank accession No. EAW66403.1, GenBank accession No. AAQ63403.1, GenBank accession No. AAB34148.1, GenBank accession No. AAH47896.1, GenBank accession No. NP_001619.1, GenBank accession No. 2PD5_A, GenBank accession No. AAF72885.1, GenBank accession No. NP 653280.1, GenBank accession No. BAF83085.1, GenBank accession No. AAH70129.1, GenBank accession No. 1X71_A, GenBank accession No. BAB55338.1, GenBank accession No. EAW68058.1, GenBank accession No. BAF85629.1, GenBank accession No. BAB70777.1, GenBank accession No. NP_109591.1, GenBank accession No. AAD22767.1, GenBank accession No. BAC04252.1, GenBank accession No. EAW47735.1 and GenBank accession No. EAW97581.1; and (b) measuring expression levels of at least one protein in the step (a) or the polynucleotide encoding each of the proteins, wherein when the high-expression of the at least one protein or the polynucleotide encoding each of the proteins is decreased, the test substance is determined as the therapeutic substance for preventing or treating pancreatic cancer.

The present inventors have found that unlike common pancreatic cancer cells, the expression level of the protein selected from the group consisting of the proteins described above or the polynucleotide encoding each of the proteins was significantly increased in pancreatic cancer stem cells, indicating that it is an essential element for the survival of cancer stem cells. Therefore, a test substance having an inhibitory effect to the expression may induce to growth inhibitory and apoptosis in cancer stem cells, whereby the test substance is determined as the therapeutic substance for preventing or treating pancreatic cancer.

As the therapeutic agents identified by the present screening method target not only common cancer cells but also pancreatic cancer stem cells which drive carcinogenesis, maintenance and recurrence with rare population, it enables to fundamentally treat pancreatic cancer.

In still further aspect of this invention, there is provided a pharmaceutical composition for preventing or treating cancer comprising as an active ingredient an inhibitor against the GLRX3 (Glutaredoxin-3) activity or expression.

According to a preferred embodiment, the present pharmaceutical composition includes (a) a therapeutically effective amount of an inhibitor against the GLRX3 (Glutaredoxin-3) activity or expression described above; and (b) a pharmaceutically acceptable carrier. The term "therapeutically effective amount" as used herein means an amount sufficient to achieve the effect or activity of an inhibitor against the GLRX3 (Glutaredoxin-3) activity or expression.

When the composition of the present disclosure is prepared as a pharmaceutical composition, the pharmaceutical composition of the present disclosure may comprise a pharmaceutically acceptable carrier. The pharmaceutical composition may contain a pharmaceutically acceptable carrier. In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition according to the present invention may be administered orally or parenterally, i.e., by intravenous, subcutaneous, intramuscular, intraperitoneal, transdermal, mucosal or local administration, and preferably parenterally.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Generally, the pharmaceutical composition of the present invention may be administered with a daily dose of 0.0001-100 mg/kg.

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

The inhibitor against the GLRX3 (Glutaredoxin-3) activity or expression used in the present decreases the number of cells expressing cancer stem cell markers CD24, CD44 and ESA, and it decreases also cell proliferation rate and migration potential. In addition, it leads to decrease of sphere formation, whereby the cancer stem cell proliferation recognized as an early stage of carcinogenesis may be inhibited.

The inhibitor against the GLRX3 (Glutaredoxin-3) activity used in the present is antibodies or peptides which is specifically bound to GLRX3, low molecular weight compounds or natural extractions.

The antibody used in the present invention is polyclonal or monoclonal antibody, preferably monoclonal antibody. Antibody production may be prepared by a method widely known in the art, such as a hybridoma method (Kohler and Milstein, European Journal of Immunology, 6:511-519 (1976)), a recombinant DNA methods (U.S. Pat. No. 4,816,56) or a phage antibody library technique (Clackson et al, Nature, 352:624-628 (1991) and Marks et al, J. Mol. Biol., 222:58, 1-597 (1991)). General process for antibody production is described in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; Coligan, CURRENT PROTOCOLS IN IMMUNOLOGY, Wiley/Greene, NY, 1991, and the literatures are inserted as reference in the present invention. For example, the preparation of the hybridoma cells producing monoclonal antibody is accomplished by fusing immortalized cell line with antibody-producing lymphocytes. The technology required for this process is widely known in the art and may be easily carried out using techniques. Polyclonal antibodies may be produced by injecting the protein antigen into an appropriate animal and collecting blood samples from the animal to obtain sera containing antibodies using affinity technology known in the art.

The peptide that specifically binds to the GLRX3 to inhibit its activity may be obtained by the typical method known in the art, for example, by phage display (Smith G P, "Filamentous fusion phage: novel expression vectors that display cloned antigens on the virion surface". Science 228 (4705): 1315-1317 (1985); Smith G P, Petrenko V A, "Phage display". Chem. Rev. 97 (2):391-410 (1997)).

The low molecular weight compound inhibiting the GLRX3 activity may be easily obtained by the screening method described below.

The inhibitor against the GLRX3 (Glutaredoxin-3) expression used in the present invention is anisense oligonucleotides, siRNA oligonucleotides or shRNA oligonucleotides specifically binding to the GLRX3 gene.

As used herein, the term "antisense oligonucleotide" means DNA or RNA or derivatives thereof containing a nucleic acid sequence complementary to a particular mRNA sequence, and binds to the complementary sequence within mRNA to inhibit translation of mRNA into protein. The antisense oligonucleotide sequence may be a DNA or RNA sequence that is complementary to the GLRX3 mRNA, and is able to bind to the GLRX3 mRNA, and it is able to inhibit translation, cytoplasmic translocation, or maturation of the GLRX3 mRNA or all other activities essential for overall biological functions. The antisense oligonucleotide has a length of 6 to 100 bases, preferably 8 to 60 bases, and more preferably 10 to 40 bases.

The antisense oligonucleotide may be modified at one or more positions of the bases, sugars or backbones in order to have improved effectiveness (De Mesmaeker et al., Curr Opin Struct Biol., 5 (3): 343-55 (1995)). The oligonucleotide backbone may be modified, for example, with phosphorothioates, phosphotriesters, methyl phosphonates, short chain alkyl, cycloalkyl, or short chain heteroatomic or heterocyclic intersugar linkages. Also, the antisense oligonucleotide may contain one or more substituted sugar moieties. The antisense oligonucleotide may also contain modified bases. Examples of the modified bases include hypoxanthine, 6-methyladenine, 5-methylpyrimidines (especially, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hyroxymethyluracil, 8-azaguanine, 7-deazaguanine, N6 (6-aminohexyl) adenine, and 2,6-diaminopurine. In addition, the antisense oligonucleotide of the present invention may be chemically bonded to one or more moieties or conjugates enhancing the activity and cellular uptake of the antisense oligonucleotide. For example, liphophilic moieties include, but are not limited to, a cholesterol moiety, a cholesteryl moiety, cholic acid, a thioether, a thiocholesterol, an aliphatic chain, a phospholipid, a polyamine chain, a polyethylene glycol chain, adamantane acetic acid, a palmityl moiety, an octadecylamine moiety and a hexylamino-carbonyl-oxycholesterol moiety. A method of preparing oligonucleotides including lipid moieties is well known in the art (U.S. Pat. Nos. 5,138,045, 5,218,105 and 5,459,255). The modified oligonucleotide may have enhanced stability in the presence of nucleases and enhanced binding affinity to target mRNA.

The antisense oligonucleotide may be synthesized in vitro by an ordinary method and administered to the body, or may be synthesized in vivo. A method for synthesizing antisense oligonucleotide in vitro employs RNA polymerase I. A method for synthesizing antisense RNA in vivo involves performing transcription of antisense RNA using a vector containing a multicloning site (MCS) in the opposite direction. Such antisense RNA preferably contains a translation stop codon in its sequence to block translation into a peptide sequence.

Design of the antisense oligonucleotide useful in the present invention may be easily performed by the method known in the art with reference to the nucleotide sequence as set forth in SEQ ID NO:1 (Weiss, B. (ed.): Antisense Oligodeoxynucleotides and Antisense RNA: Novel Pharmacological and Therapeutic Agents, CRC Press, Boca Raton, Fla., 1997; Weiss, B., et al., Antisense RNA gene therapy for studying and modulating biological processes. Cell. Mol. Life. Sci., 55:334-358 (1999).

According to a preferred embodiment, the inhibitor against GLRX3 expression is siRNA or shRNA comprising a complementary sequence to GLRX3 gene.

As used herein, the term "siRNA" refers to a nucleic acid molecule that is able to mediate RNA interference or gene silencing (reference: WO 00/44895, WO 01/36646, WO 99/32619, WO 01/29058, WO 99/07409 and WO 00/44914). Since siRNA can suppress the expression of the target gene, it provides an effective way of gene knockdown or genetic therapy. First discovered in plants, worms, fruit flies and parasites, siRNA has been recently developed and used for studies of mammalian cells.

In the case in which the siRNA molecule is used in the present invention, it may have a structure in which its sense strand (a sequence corresponding to the p53 mRNA sequence) and its antisense strand (a sequence complementary to the p53 mRNA sequence) form a double strand. Alternatively, it may have a single-stranded structure having self-complementary sense and antisense strands.

The siRNA is not limited to those in which double-stranded RNA moieties constitute complete pairs, but includes the unpaired moieties such as mismatch (corresponding bases are not complementary), bulge (no corresponding base in one chain), etc. The total length of the siRNA may be 10 to 100 bases, preferably 15 to 80 bases, more preferably 20 to 70 bases.

The end of the siRNA may be either blunt or cohesive as long as it is capable of suppressing the expression of the p53 gene via RNAi. The cohesive end may be either 3'- or 5'-cohesive end.

In the present invention, the siRNA molecule may have a short nucleotide sequence (e.g., about 5-15 nucleotides) inserted between the self-complementary sense and antisense strands. In this case, the siRNA molecule formed from the expression of the nucleotide sequence forms a hairpin structure via intramolecular hybridization, resulting in a stem-and-loop structure overall. The stem-and-loop structure is processed in vitro or in vivo to give an activated siRNA molecule capable of mediating RNAi.

According to a preferred embodiment, the siRNA of the present invention is a complementary sequence to the nucleotides 591-616 as set forth in SEQ ID NO:1 of the GLRX3 gene, and siRNA as set forth in SEQ ID NOs:2 and 3. The shRNA of the present invention is a complementary sequence to the nucleotides 496-516 as set forth in SEQ ID NO:1 of the GLRX3 gene, and shRNA as set forth in SEQ ID NO:4.

The term "active ingredient" as used herein means an amount sufficient to achieve the effect or activity of an inhibitor against the GLRX3 (Glutaredoxin-3) activity or expression. The quantitative limit of the inhibitor against the GLRX3 (Glutaredoxin-3) activity or expression included in the present composition may be selected in relevant ranges by a person having an ordinary skill in the art to perform.

In the present pharmaceutical composition for preventing or treating cancer, preferably the cancer is caused by a cancer stem cell, and more preferably the cancer is pancreatic cancer.

In still further aspect of this invention, there is provided a method for inhibiting proliferation of a cancer cell comprising: inhibiting the activity or expression of the GLRX3 (Glutaredoxin-3).

Preferably, the cancer cell is a cancer stem cell.

In further aspect of this invention, there is provided a method for preventing or treating cancer comprising, administering to a mammalian subject in need thereof a therapeutically effective amount of an inhibitor against the GLRX3 (Glutaredoxin-3) activity or expression.

Preferably, the cancer is pancreatic cancer.

The features and advantages of the present invention will be summarized as follows:

(a) The present invention provides a novel molecular marker for pancreatic cancer stem cells and pancreatic cancer, to a marker detection method, and to a screening method.

(b) The present invention is a marker discovered from the pancreatic cancer cell lines, wherein the marker may detect pancreatic cancer, in particular an early stage of pancreatic cancer, through the detection of a pancreatic cancer stem cell marker.

(c) In addition, the marker of the present invention may enable an accurate diagnosis and prognosis analysis of pancreatic cancer

BRIEF DESCRIPTION OF THE DRAWINGS

FIG. 2a represents results that Notch, Hedgehog and wnt signaling known as cancer stem cell signaling pathways in Hpac-spheres were activated as compared to the adhesive Hpac cells. FIG. 2b represents results that oct4 and nanog which represent multipotency of stem cell, and cancer stem cell marker ABCG2 were over-expressed.

FIG. 4a is images showing sphere formation inhibitory effects by the stem cell signaling inhibitors. FIG. 4b is graphs showing differences of sphere diameters in sphere formation inhibitory effects by the stem cell signaling inhibitors. FIG. 4c is graphs showing the number of spheres in sphere formation inhibitory effects by the stem cell signaling inhibitors. Based on these results, it could be determined that sphere formations were inhibited, and sphere diameters and the number of spheres were reduced by the stem cell signaling inhibitors.

FIGS. 5a-c represent results of verification for tumorigenicities of adhesive Hpac cells and Hpac-spheres. FIG. 5a is images showing formations of pancreatic cancers and pulmonary metastasis in the NOD/SCID mouse. FIG. 5b is images of H&E immunostaining in mouse pancreas and organs occurred metastasis. FIG. 5c is graphs showing differences of cancer sizes in adhesive Hpac cells and Hpac-spheres. Adhesive Hpac cells and Hpac-spheres were in situ-transplanted into pancreas of NOD/SCID mice (Charles River, Japan) and observed to tumorigenicities. As a result, the Hpac-spheres injected group showed higher tumorigenic potential than that of the adhesive Hpac cells injected group, and metastasis into other organs.

FIG. 6 represents results of expression verifications of the identified secretory proteins in media of adhesive Hpac cells, Hpac-spheres, adhesive Capan 1 cells and Capan 1-spheres through western blot. It could be determined that AKR1B1, HSP90, ALDH, Vimentin and GLRX3 were over-expressed in media of Hpac-spheres and Capan 1-spheres.

FIG. 7 represents results of verification on expressions of mRNA and protein of GLRX3 in eight pancreatic cancer cell lines (AsPC-1, BxPC-3, Capan-1, Capan-2, Cfpac-1, HPAC, Panc-1 and Miapaca-2) and HPDE (Human Pancreatic Ductal Epithelial cell).

FIGS. 10a-b represent results of verifications on expression changes by GLRX3 inhibition in GLRX3 knock-down cell line. FIG. 10a represents results of western blot in expressions of mRNA and protein of GLRX3. FIGS. 10b-c represent results of verifications on cell proliferation rates.

FIG. 11a represents results of verifications on ability to form spheres of the GLRX3 k/d cell line. FIG. 10b represents results of verifications on cell viability and proliferation rates.

FIG. 15a represents western blot results on expression of MSK2 protein. FIG. 15b represent results that western blot results of MSK2 protein are shown as graphs by measuring using densitometry. It was high-expressed in pancreatic cancer patient serum as compared to normal serum.

FIG. 16a represents western blot results of expression on vimentin protein. FIG. 16b represents results that western blot results of vimentin protein are shown as graphs by measuring using densitometry. It was high-expressed in pancreatic cancer patient serum as compared to normal and chronic pancreatitis patient sera.

FIG. 17a represents western blot results of expression on ALDH protein. FIG. 17b represents results that western blot results of ALDH protein are shown as graphs by measuring using densitometry. It was high-expressed in pancreatic cancer patient serum as compared to normal and chronic pancreatitis patient sera.

FIGS. 18a-b represent results of expression verifications of GLRX3 protein through western blot after detection of sera in normal, chronic pancreatitis patient and pancreatic cancer patient using MARS. FIG. 18a represents western blot results of expression on GLRX3 protein. FIG. 18b represents results that western blot results of GLRX3 protein are shown as graphs by measuring using densitometry. It was high-expressed in pancreatic cancer patient serum as compared to normal and chronic pancreatitis patient sera.

FIG. 19a represents comparison results on GLRX3 expression in bloods of normal control, chronic pancreatitis patient and pancreatic cancer patient. FIG. 19b is graphs of comparisons on survival period between patients with more than 1800 ng/mL of GLRX3 level and patients with less than 1800 ng/mL of GLRX3 level.

DETAILED DESCRIPTION

Figure 1:
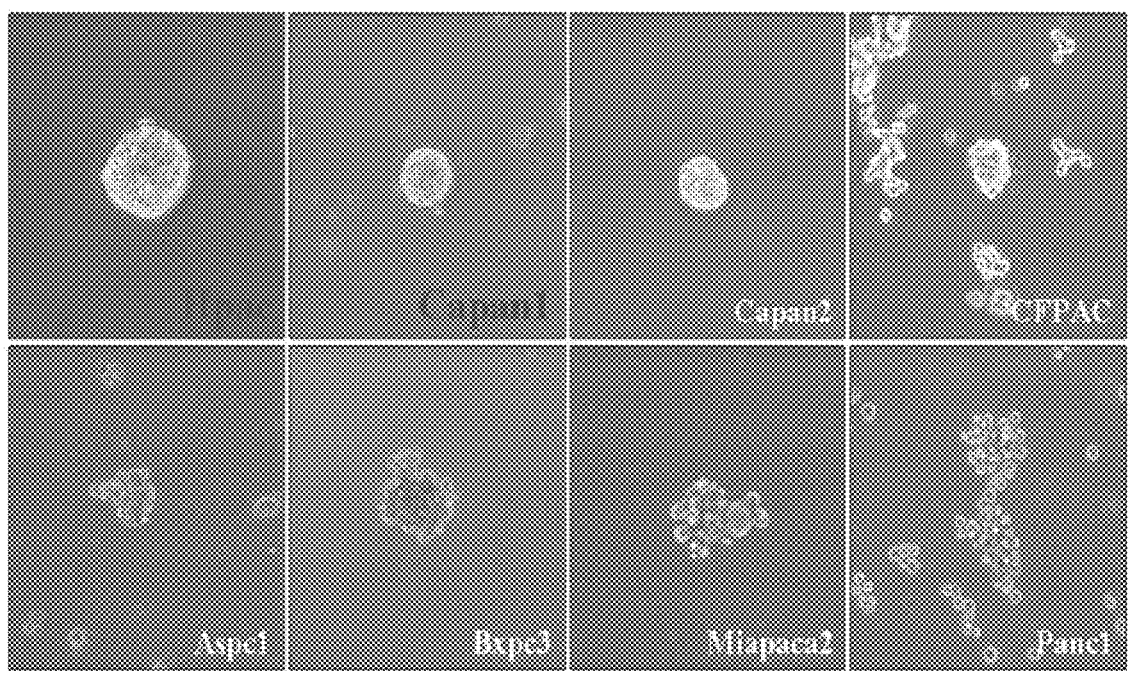
FIG. 1 represents results of sphere-culture in pancreatic cancer cell lines (Hpac, CAPAN1, CAPAN2, CFPAC, ASPC1, BXPC3, MIAPACA2 and PANC1). It shows sphere formations in Hpac, CAPAN1 and CAPAN2.

The present invention will now be described in further detail by examples. It would be obvious to those skilled in the art that these examples are intended to be more concretely illustrative and the scope of the present invention as set forth in the appended claims is not limited to or by the examples.

Examples

Unless otherwise described in the specification, solid/solid, solid/liquid and liquid/liquid indicate (weight/weight) parts by weight or %, (weight/volume) parts by weight or %, and (volume/volume) parts by weight or %, respectively.

Materials and Methods

Isolation and Culture of Sphere Having Properties of Cancer Stem Cells from Human Pancreatic Cancer Cell Lines Eight pancreatic cancer cell lines (Hpac, Aspc1, Bxpc3, Capan1, Capan2, CFPAC, Miapaca2, and Panc 1) were purchased from the American Type Culture Collection (ATCC, Manassas, Va., US) and cultured in media according to the protocol of ATCC instructions. i.e., AsPC-1 and BxPC-3 cell lines were cultured in RPMI1640 (Invitrogen Gibco, Grand Island, N.Y.) supplemented with 10% fetal bovine serum (FBS, HyClone, Logan, Utah, US). Capan-1 and CFPAC-1 cell lines were cultured in IMDM (Invitrogen Gibco) supplemented with 10% FBS. Capan-2 cell line was cultured in McCoy's 5a (Invitrogen Gibco) supplemented with 10% FBS. MIA PaCa-2 cell line was cultured in DMEM (Invitrogen Gibco) supplemented with 10% FBS and 2.5% horse serum (Hyclone). Hpac cell line was cultured in DMEM/Ham's F12 (D/F12; Invitrogen Gibco) supplemented with 10% FBS. PANC-1 cell line was cultured in DMEM supplemented with 10% FBS.

For sphere formation, pancreatic cancer cell lines were plated 1000 cell/mL in serum-free DMEM/F12 supplemented with EGF (10 ng/mL, R&D Systems Inc., Minneapolis, Minn.), bFGF (10 ng/µL, R&D Systems Inc.), 1 ITS (insulin transferring selenium, Gibco) and 0.5% FBS on Corning Costar ultra-low attached 6-well culture dishes (Corning Inc., Corning, N.Y., US), and cultured for 7-10 days. The adherent cells cultured with the same media by attaching on culture plates (Nalgene Nunc Int., Rochester, N.Y.) were used as a control group.

Expression Analysis of Cancer Stem Cell-Related Genes in Sphere Cells

Total RNA was extracted with RNeasy mini prep kit (Qiagen, Valencia, Calif., US). Each 2 μL of RNA was reverse-transcribed using SuperScript II (Gibco BRL, Grand Island, N.Y.) at 42° C. for 1 hour. Expressions of cancer stem cell-related genes were analyzed by PCR using primers and Taq DNA polymerase (Takara Biochemicals, Tokyo, Japan). Expression of Beta-actin gene was used as a control. The primers, PCR temperature and cycles are described in Table 1.

Inhibition of Sphere Formation by Stem Cell Signaling Inhibitors

Well-known stem cell signaling inhibitors DAPT (Calbiochem, San Diego, Calif., USA), Cyclopamine-KAAD (Calbiochem, San Diego, Calif., USA), LiCl (Sigma-Aldrich, Inc., St. Louis, Mo.), ATRA (Sigma-Aldrich, Inc., St. Louis, Mo.), OV (Sigma-Aldrich, Inc., St. Louis, Mo.) were added added into sphere culture medium, and cultured. After 7 days, sphere formation was observed.

TABLE 1

| Gene | Forward primer sequence (5'-3') | Reverse primer sequence (5'-3') | Tm/cycle |
|---|---|---|---|
| Jagged 1 | CTCAATTACTGTGGGACTCATCA | GAACACTCACACTCAAAGCCC | 52° C./30 |
| Notch3 | ATGGTGGGAACTAAACACAGCT | ATGACCCTGGAGGAAGCACA | 55° C./35 |
| Hes1 | GTGCTGTCTGGATGCGGAGT | GAACACTCACACTCAAAGCCC | 55° C./35 |
| Ihh | CCTGAACTCGCTGGCTATCT | AATACACCCAGTCAAAGCCG | 56° C./35 |
| PTCH | GCAGTGGTGAGAGAAAAGGA | CTCGGATTGGTGACCATAAG | 59° C./30 |
| Gli1 | AGAGTCCAGGGGGTTACATA | AGAGTCCAGGGGGTTACATA | 57° C./35 |
| Wnt4 | CTCCTCGTCTTCGCCGTCTT | TACTGGCACTCCTCAATGGA | 62° C./40 |
| Dvl2 | GGTTGGGGAGACGAAGGTGATT | ATCTGAGGACACCAGCCAGGATAC | 58° C./30 |
| Lef1 | CGAAGAGGAAGGCGATTTAG | GGATGGGTGGAGAAAGAGAT | 62° C./40 |
| Oct4 | GTGGAGGAAGCTGACAACAA | AGCAGCCTCAAAATCCTCTC | 62° C./27 |
| Nanog | ACTGTCTCTCCTCTTCCTTCCT | AGAGTAAAGGCTGGGGTAGGTA | 61° C./30 |
| Stat3 | GTCTGGCTGGACAATATCAT | TTGGGAATGTCAGGATAGAG | 56° C./30 |
| ABCG2 | TATGAGTGGCTTATCCTGCT | CACTGATCCTTCCATCTTGT | 56° C./30 |
| PTEN | GGACGAACTGGTGTAATGAT | CAGACCACAAACTGAGGATT | 56° C./30 |
| Beta-actin | GGCATCCTCACCCTGAAGTA | GGGGTGTTGAAGGTCTCAAA | 55° C./25 |

Expression Analysis of Cancer Stem Cell Markers in Sphere Cells Through Fluorescence-Activated Cell Sorting After incubations of adhesive Hpac cells and Hpac-spheres, cells were treated with accutase (Sigma-Aldrich, St. Louis, Mo.) to prepare suspensions with the same number of single cells. Afterward, adhesive cells and spheres were stained with cancer stem cell marker antibodies as follows: FITC-CD44 (BD Biosciences PharMingen, San Diego, Calif.), PE-PROM2 (BD Biosciences PharMingen, San Diego, Calif.), PE-EphA2 (BD Biosciences PharMingen, San Diego, Calif.), PE-CD130 (BD Biosciences PharMingen, San Diego, Calif.), PE-CD271 (BD Biosciences PharMingen, San Diego, Calif.), PE-CD24 (BD Biosciences PharMingen, San Diego, Calif.), PE-CD133 (BD Biosciences PharMingen, San Diego, Calif.) and PE-CD117 (BD Biosciences PharMingen, San Diego, Calif.).

Fluorescence-Activated Cell Sorting was carried out using BD LSR II (BD Biosciences, Franklin Lakes, N.J.) and analyzed by BD FACSDiva software.

Verification for Tumorigenicity of Hpac-Spheres

Adhesive Hpac cells and Hpac-spheres were treated with 0.25% trypsin EDTA (Gibco BRL, Grand Island, N.Y.) to prepare suspensions with the same number of single cells. Afterward, they were directly in situ-transplanted into pancreas of NOD/SCID mice (Charles River, Japan) and observed to tumorigenicity of Hpac cells and Hpac-spheres.

Analysis of Cancer Stem Cell-Related Secretory Proteins in Sphere Cells

In order to analyze cancer stem cell-related secretory protein in media of sphere cells, Hpac cells and Capan 1 cells were prepared to spheres or adherent cells for 7-10 days. Then, their media were changed to serum-free DMEM/F12 (Gibco BRL, Grand Island, N.Y.) and they were incubated 24 hours. The culture media supernatants of spheres and adherent cells were collected using centrifugation and filter.

The supernatants containing various secretory proteins were concentrated using amicon ultra centifugal filter device with 3 kDa molecular-mass cut off (MWCO), and carried out to proteomics analysis (2-D gel analysis and MALDI-TOF). Spots showing differences after stained gel image analysis were cutted off, and identified through MALDI-TOF (matrix assisted laser desorption/ionization-time of flight) analysis. MASCOT was used as the database search engine (Na K et al., *Proteomics* (9):3989-3999, 2009).

Expression Analysis of Pancreatic Cancer Stem Cell-Related Secretory Proteins in Sphere Cell Media Through Western Blot In order to verify expressions of secretory proteins identified by proteomics analysis in the media of adhesive Hpac cells, Hpac-spheres, adhesive Capan 1 cells and Capan 1-spheres, the media supernatants were collected using centrifugation and filter.

The supernatants were concentrated using amicon ultra centifugal filter device with 3 kDa molecular-mass cut off (MWCO) to quantify proteins. Each of 25 µg of the quantified proteins was loaded into 10% SDS-polyacrylamide gel and electrophorezed. The proteins fractionized by size using the electrophoresis were transferred onto PVDF membranes (Millipore corporation, Billerica, Mass., USA). To reduce nonspecific binding, the membranes were blocked for 1 hour in TBS-T buffer (Tris-buffered saline/0.05% Tween-20) containing 5% non-fat milk. Then, each membrane was incubated with the primary antibody corresponding to secretory proteins identified by proteomics analysis at 4° C. for overnight. The primary antibodies were mouse monoclonal AKR1B1 (santa cruz biotechnology Inc, santa cruz, CA), rabbit polyclonal HSP90 (santa cruz biotechnology Inc, santa cruz, CA), mouse monoclonal ALDH (BD Biosciences PharMingen, San Diego, Calif.), mouse monoclonal vimentin (santa cruz biotechnology Inc, santa cruz, CA) and mouse monoclonal GLRX3 (Abnova corporation, Taipei). The membrane was washed with TBS-T buffer, and incubated with HRP (horseradish peroxidase)-conjugated secondary antibody (santa cruz biotechnology Inc, santa cruz, CA) for 1 hour. Each protein was detected using Enhanced chemiluminescence system (PIERCE, Rockford, Ill.).

Verification on Expressions of mRNA and Protein of GLRX3 in Pancreatic Cancer Cell Lines To verify GLRX3 expression, mRNA and protein were extracted in eight pancreatic cancer cell lines (AsPC-1, BxPC-3, Capan-1, Capan-2, Cfpac-1, HPAC, Panc-1 and Miapaca-2) and HPDE (Human Pancreatic Ductal Epithelial cell). Total RNA was extracted with RNeasy mini prep kit (Qiagen, Valencia, Calif., US), and reverse-transcribed using SuperScript II (Gibco BRL, Grand Island, N.Y.). Expressions of GLRX3 gene in pancreatic cancer cell lines were analyzed by PCR using GLRX3 primers and Taq polymerase. Expression of Beta-actin gene was used as a control. Expression analysis of GLRX3 protein in pancreatic cancer cell lines was performed in total proteins and secretory proteins. Total proteins were extracted using cell lysis buffer (50 mM Tris, 150 mM NaCl, 25 mM β-glycerophosphate, 25 mM NaF, 0.5 M EDTA, 1% NP-40, 0.1 mM PMSF, 1% protease inhibitors cocktail (Roche)). Secretory proteins were prepared as follows: culture media cultured under serum-free condition were centrifuged to remove cell debris, and precipitated by ice-cold acetone in the final volume of 80%. The precipitated secretory proteins were washed with 100% ice-cold acetone, dried by centrifugal vacuum dryer, and dissolved in cell lysis buffer. Total proteins and secretory proteins were quantified. Each of 25 ng of the quantified proteins was loaded into 10% SDS-polyacrylamide gel and electrophorezed. The proteins fractionized by size using the electrophoresis were transferred onto PVDF membrane (Millipore corporation, Billerica, Mass., USA). To reduce nonspecific binding, the membrane was blocked for 1 hour in TBS-T buffer (Tris-buffered saline/0.05% Tween-20) containing 5% non-fat milk. Then, the membrane was incubated with the primary antibody to GLRX3 (Abnova corporation, Taipei, China) at 4° C. for overnight. The membrane was washed with TBS-T buffer, and incubated with HRP (horseradish peroxidase)-conjugated secondary antibody (santa cruz biotechnology Inc, santa cruz, CA, USA) for 1 hour. The protein was detected using West Pico chemiluminescent Substrate system (PIERCE, Rockford, Ill.).

Verification on Over-Expression of GLRX3 in the Cell Fraction Having Properties of Pancreatic Cancer Stem Cells To fractionize cells having properties of cancer stem cells, Hpac and CFPAC-1 cell lines were treated with accutase (Sigma-Aldrich, St. Louis, Mo.) to prepare suspensions with the same number of single cells. Afterward, the cells were stained on ice for 10 min with cancer stem cell marker as follows: PE-CD24 (BD Biosciences PharMingen, San Diego, Calif.), APC-CD44 (BD Biosciences PharMingen, San Diego, Calif.) and FITC-ESA (BD Biosciences PharMingen, San Diego, Calif.). In addition, the cells were stained with purified mouse IgG1, λ-FITC, IgG2a, κ-PE and IgG2b, κ-APC (BD Biosciences PharMingen, San Diego, Calif., USA) as isotype controls to antibodies. Fluorescence-Activated Cell Sorting was carried out using FACSAria II (BD Immunocytochemistry system, Franklin Lakes, N.J., US). Each total RNA of fractions in cells expressing 3 types of markers (CD24+/CD44+/ESA+) and cells non-expressing 3 types of markers (CD24−/CD44−/ESA−) was extracted with RNeasy mini prep kit (Qiagen, Valencia, Calif.), and reverse-transcribed using SuperScript II (Gibco BRL, Grand Island, N.Y., US). Expressions of GLRX3 gene were analyzed by PCR using GLRX3 primers and Taq polymerase. Expression of Beta-actin gene was used as a control.

To inhibit GLRX3, siRNA (invitrogen Stealth™ siRNA duplex oligoribonucleotides) to GLRX3 was used. Sense siRNA sequence was UGA GGG AGU UCU UUA GCU AAC UCU G, and antisense siRNA sequence was CAG AGU UAG CUA AAG AAC UCC CUC A. Med GC (invitrogen) was used as negative control siRNA. CFAPC-1 cells were transfected with GLRX3 or negative control siRNA using RNAiMAX (invtirogen, Carlsbad, Calif., US), and incubated for 72 hours. The cells were treated with accutase (Sigma-Aldrich, St. Louis, Mo.) to prepare suspensions with the same number of single cells. Afterward, the cells were stained with PE-CD24 (BD Biosciences PharMingen, San Diego, Calif.), APC-CD44 (BD Biosciences PharMingen, San Diego, Calif.) and FITC-ESA (BD Biosciences PharMingen, San Diego, Calif.). Fluorescence-Activated Cell Sorting was carried out using BD LSR II (BD Biosciences, Franklin Lakes, N.J.) and analyzed by BD FACSDiva software.

GLRX3 Knock-Down Cell Line Establishment and Characterization

To verify inhibitory effects of GLRX3 expression, shRNA (SABiosciences Sure Silencing™ shRNA plasmid) to GLRX3 and control shRNA were prepared. Hpac cell line was transfected with the shRNAs to establish GLRX3 knockdown (k/d) cell line. Expressions of GLRX3 mRNA and protein were investigated. shRNA sequence to GLRX3 was GTG GAA ATT CTT CAC AAA CAT, and control shRNA sequence was GGA ATC TCA TTC GAT GCA TAC. Selection marker was puromycin (2.0 ng/mL). At one day before gene transfection, an equal number of cells were attached on the plates. Then, shRNA to GLRX3 and control shRNA were mixed with Lipofectamine-2000 (Invitrogen, Carlsbad, Calif., USA) to transfect the cells. At 24 hours after gene transfection, the media were changed to media containing 2 ng/mL of puromycin, and maintained for 3 days. Survival cells in media containing puromycin were plated 1 cell/well on 96-well plate, and cultured. mRNA and protein of the cells proliferated in each well were extracted, and GLRX3 expression changes were investigated by PCR and western blot, whereby two clones of the GLRX3 k/d cell line and two clones of the control were finally obtained. In order to verify cancer-related characteristic changes of the obtained GLRX3 k/d, doubling time assay and wound-healing assay were carried out. For cell doubling times, $1.25 \times 10^4$ cells were seeded into 24-well plate. The cells were detached by 0.25% trypsin-EDTA and counted every a regular hour for 5 days using hematocytometer. For wound-healing assay, the cells were grown until nearly 100% confluent, and linear wound was created in the confluent monolayer using pipette tip. Wound healing ability was observed according to time under a microscope, and photographed (Olympus DP50).

Analysis of Cancer Stem Cell-Related Characteristic Changes in GLRX3 Knock-Down Cell Line As GLRX3 were revealed as cancer stem cell-related protein, cancer stem cell-related characteristic changes induced by the GLRX3 k/d were investigated. First, ability to form spheres of the GLRX3 k/d cell line and the control cell line was verified. To achieve this, two clones of the GLRX3 k/d cell line and two clones of the control were sphere-cultured for 7 days. For clonogenic assay, 0.6% agar in cell media was boiled, hardened on 24-well plate (lower layer media). The cells at density of 1000 cell/well and 0.3% agar-cell media (upper layer media) were mixed, and hardened on lower layer media. Once 0.3% upper layer media was hardened, 500 µL/well of media was added on the upper layer media. Adding the media every third day, the cells were cultured for 3-4 weeks. Afterward, the media on agar was removed, stained with crystal violet to count the number of colony.

Expression Analysis of Pancreatic Cancer Stem Cell-Related Secretory Proteins in Human Pancreatic Cancer Tissue Through Immunohistochemistry Pancreatic tissue slides were deparaffinized in xylene and rehydrated in a graded ethanol series. Endogenous peroxidase was blocked by immersing the slide in 0.3% hydrogen peroxide in methanol at room temperature for 20 minutes. Microwave antigen retrieval was performed in citrate buffer (0.01M, pH 6.0) for 4 min. The slides were blocked by soaking in 10% normal donkey serum in PBS for 1 hour to remove non-specific background. Then, the slides were incubated with primary antibodies in 1:200 dilution at 4° C. for overnight. The primary antibodies were mouse monoclonal AGPAT4 (Abnova corporation, Taipei), mouse monoclonal AKR1B1 (santa cruz biotechnology Inc, santa cruz, CA), rabbit polyclonal HSP90 (santa cruz biotechnology Inc, santa cruz, CA), mouse monoclonal ALDH (BD Biosciences PharMingen, San Diego, Calif.), rabbit polyclonal MSK2 (santa cruz biotechnology Inc, santa cruz, CA), mouse monoclonal Vimenti n(santa cruz biotechnology Inc, santa cruz, CA) and mouse monoclonal GLRX3 (Abnova corporation, Taipei). Subsequent reactions were carried out using Envision kit (DakoCytomation, Carpineteria, Calif., USA) according to the manufacturer's protocols. Finally, the slides were incubated with 3,3'-diaminobenzidine (DakoCytomation, Carpinteria, Calif., USA), and counterstained with Harris hematoxylin (Sigma-Aldrich, Inc., St. Louis, Mo.). The results were classified as – (negative), + (light brown), ++ (middle brown) and +++ (strong brown) according to staining intensity.

Expression Analysis of Pancreatic Cancer Stem Cell-Related Secretory Proteins in Sera of Human Normal, Chronic Pancreatitis and Pancreatic Cancer Patients Through Western Blot In sera of human normal, chronic pancreatitis and pancreatic cancer patients, expressions of pancreatic cancer stem cell-related secretory proteins were analyzed through western blot.

To verify expressions of pancreatic cancer stem cell-related secretory proteins developed in sera of human normal, chronic pancreatitis and pancreatic cancer patients, normal serum 5 cases, chronic pancreatitis serum 5 cases and pancreatic cancer serum 20 cases were selected.

After removals of 6 principal proteins (albumin, transferrin, IgG, IgA, haptoglobin and anti-trypsin) in total 30 cases of the sera using MARS (Multiple affinity removal column system), the sera were concentrated using amicon ultra centifugal filter device with 3 kDa molecular-mass cut off (MWCO) to quantify proteins. Each of 40 µg of the quantified proteins was loaded into 10% SDS-polyacrylamide gel and electrophorezed. The proteins fractionized by size using the electrophoresis were transferred onto PVDF membranes (Millipore corporation, Billerica, Mass., USA). To reduce nonspecific binding, the membranes were blocked for 1 hour in TBS-T buffer (Tris-buffered saline/0.05% Tween-20) containing 5% non-fat milk. Then, each membrane was incubated with the primary antibody (1:500 dilution) corresponding to proteins at 4° C. for overnight. The primary antibodies were rabbit polyclonal MSK2 (santa cruz biotechnology Inc, santa cruz, CA), mouse monoclonal vimentin (santa cruz biotechnology Inc, santa cruz, CA), mouse monoclonal ALDH (BD Biosciences PharMingen, San Diego, Calif.) and mouse monoclonal GLRX3 (Abnova corporation, Taipei). The membrane was washed with TBS-T buffer, and incubated with HRP (horseradish peroxidase)-conjugated secondary antibody (santa cruz biotechnology Inc, santa cruz, CA) for 1 hour. Each protein was detected using Enhanced chemiluminescence system (PIERCE, Rockford, Ill.).

Expression Verification of GLRX3 in Pancreatic Cancer Patient Blood

In order to verify expressions of GLRX3 in clinical patients (normal control patients 28 cases, chronic pancreatitis patients 9 cases and pancreatic cancer patients 57 cases), ELISA was performed using ELISA kit according to the manufacturer's protocols. The serum was diluted in PBS to 1:10 ratio to use. The standard concentrations were prepared by means of ½ serial dilution from 10 nM/mL. The diluted patient serum and standard concentrations were added into 96-well of GLRX3 ELISA kit, respectively, and incubated for 2 hours at 37° C. 100 µL, of detection reagent A was added into each well, and incubated for 1 hour at 37° C. After removals of all solutions, the wells were washed 3 times with washing buffer. 100 µL, of detection reagent B was added into each well, and incubated for 30 min at 37° C. After removal of reagent, the wells were washed 5 times, added with 90 µL of substrate solution, incubated at 37° C. for 15-20 min, added with 50 µL of stop solution, and measured the absorbance at 450 nm.

Results

Isolation and Culture of Sphere Having Properties of Cancer Stem Cells from Human Pancreatic Cancer Cell Lines Eight human pancreatic cancer cell lines were tested for the sphere formation which is property of cancer stem cell. As a result, three cancer cell lines including Hpac, Capan 1 and Capan 2 showed the ability to form the sphere. Among the sphere forming cell lines, Hpac and Capan 1 were further analyzed (FIG. 1).

Expression Analysis of Cancer Stem Cell-Related Genes in Sphere Cells

Figure 2A:
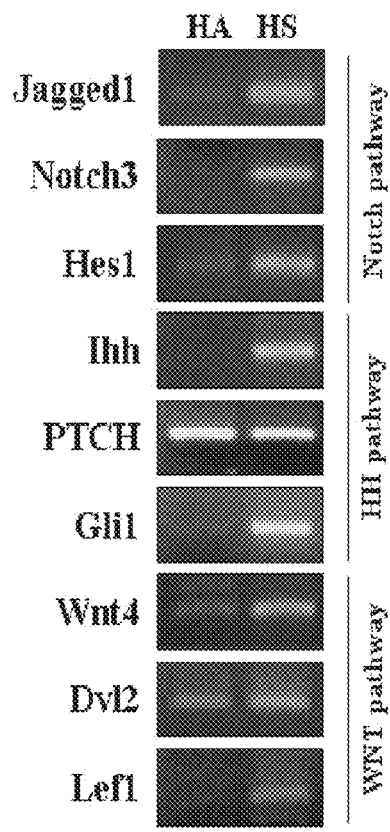
FIGS. 2a-b represent analysis results of cancer stem cell-related genes expressions in spheres.
Figure 2B:
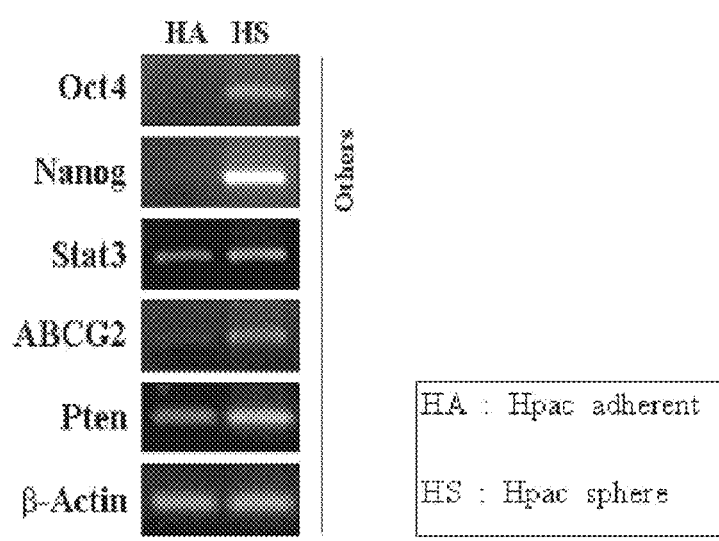

It was determined that Hpac-spheres showed greater activity of stem cell-related signaling pathways such as Notch, Hedgehog, and Wnt than that of adhesive Hpac cells. Early embryonic development related genes such as Oct4, nanog and stat3 which represent multipotency of stem cell were over-expressed. In addition, cancer stem cell markers ABCG2, PTEN were over-expressed (FIGS. 2a-b).

Figure 3:
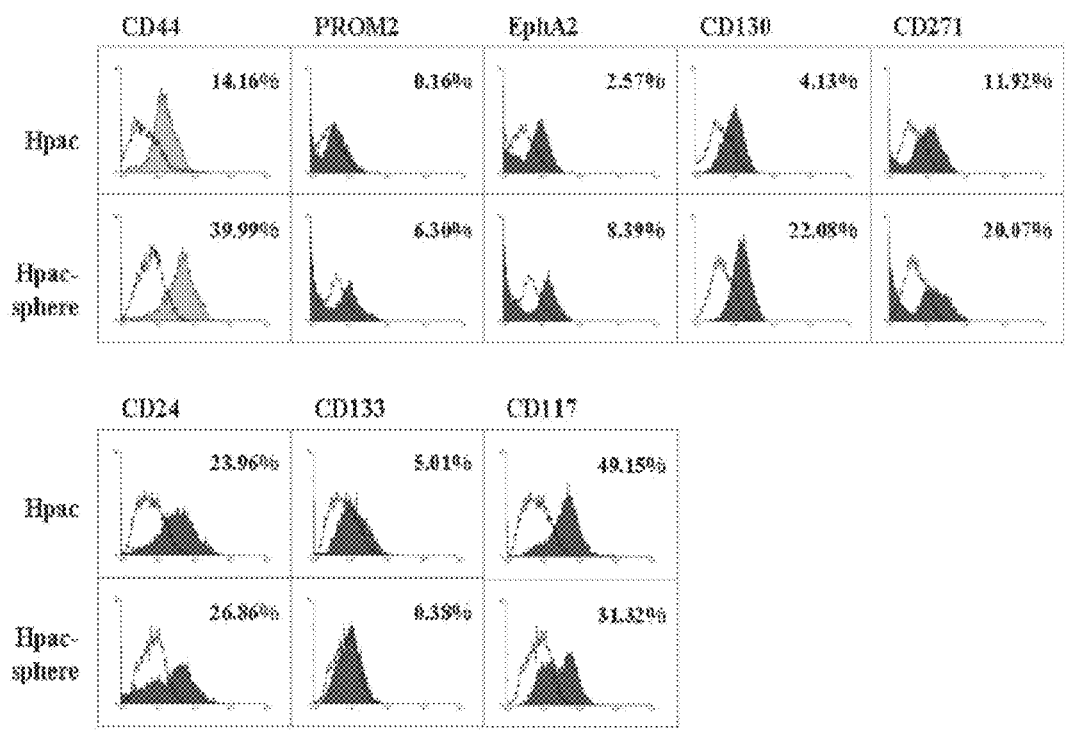
FIG. 3 represents analysis results of cancer stem cell marker expressions in spheres using Fluorescence-Activated Cell Sorting. It was determined that well-known cancer stem cell markers CD44 and PROM2 were over-expressed in adhesive Hpac cells and Hpac-spheres.

Expression Analysis of Cancer Stem Cell Markers in Sphere Cells Through Fluorescence-Activated Cell Sorting In Fluorescence-Activated Cell Sorting, it was determined that well-known cancer stem cell markers CD44, PROM2, EphA2, CD130 and CD271 were over-expressed in adhesive Hpac cells and Hpac-spheres (FIG. 3).

Inhibition of Sphere Formation by Stem Cell Signaling Inhibitors

Figure 4A:
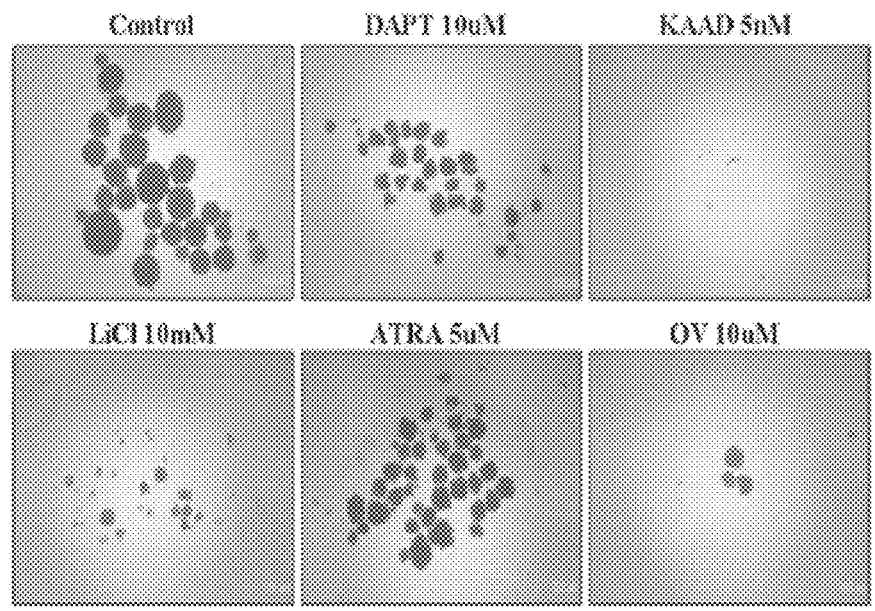
FIGS. 4a-c represent results of sphere formation inhibitory effects by well-known stem cell signaling inhibitors.
Figure 4B:
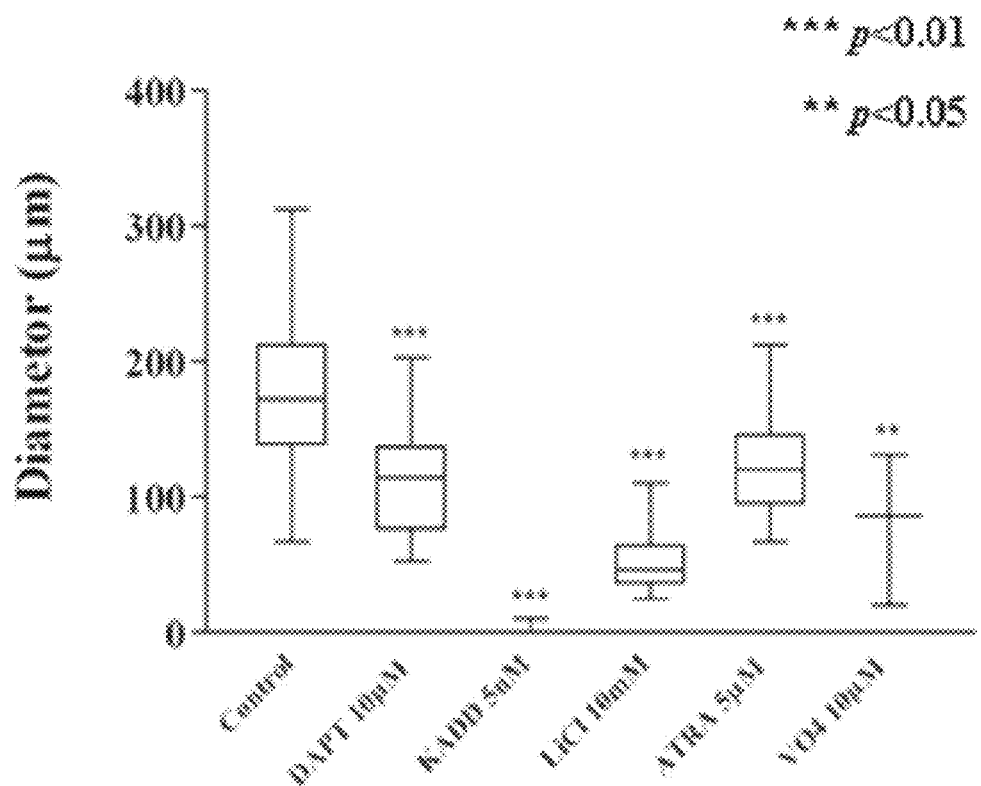
Figure 4C:
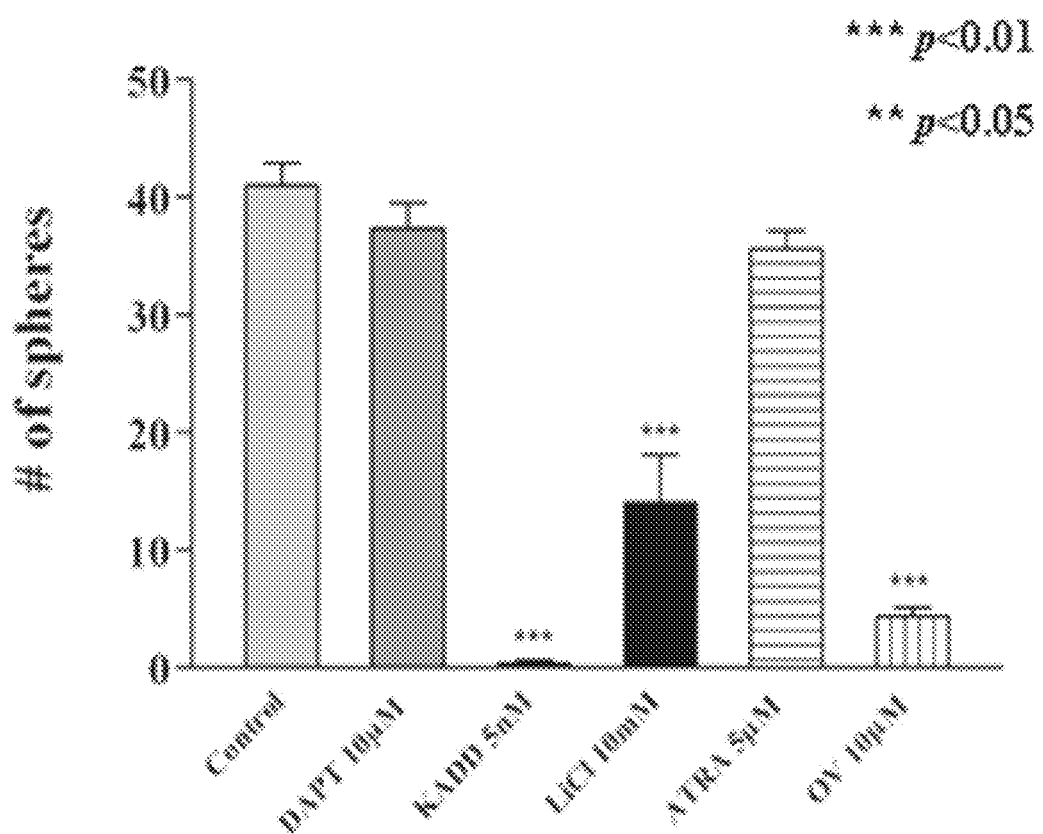

It was determined that ability to form sphere in Hpac-spheres was completely inhibited or reduced by well-known stem cell signaling inhibitors (FIGS. 4a-c; DAPT is an inhibitor to Notch; KAAD is an inhibitor to HH; LiCl is an inhibitor to GSK3b; ATRA is an inhibitor to Oct4; and OV is an inhibitor to Nanog).

Verification for Tumorigenicity of Hpac-Spheres

Figure 5B:
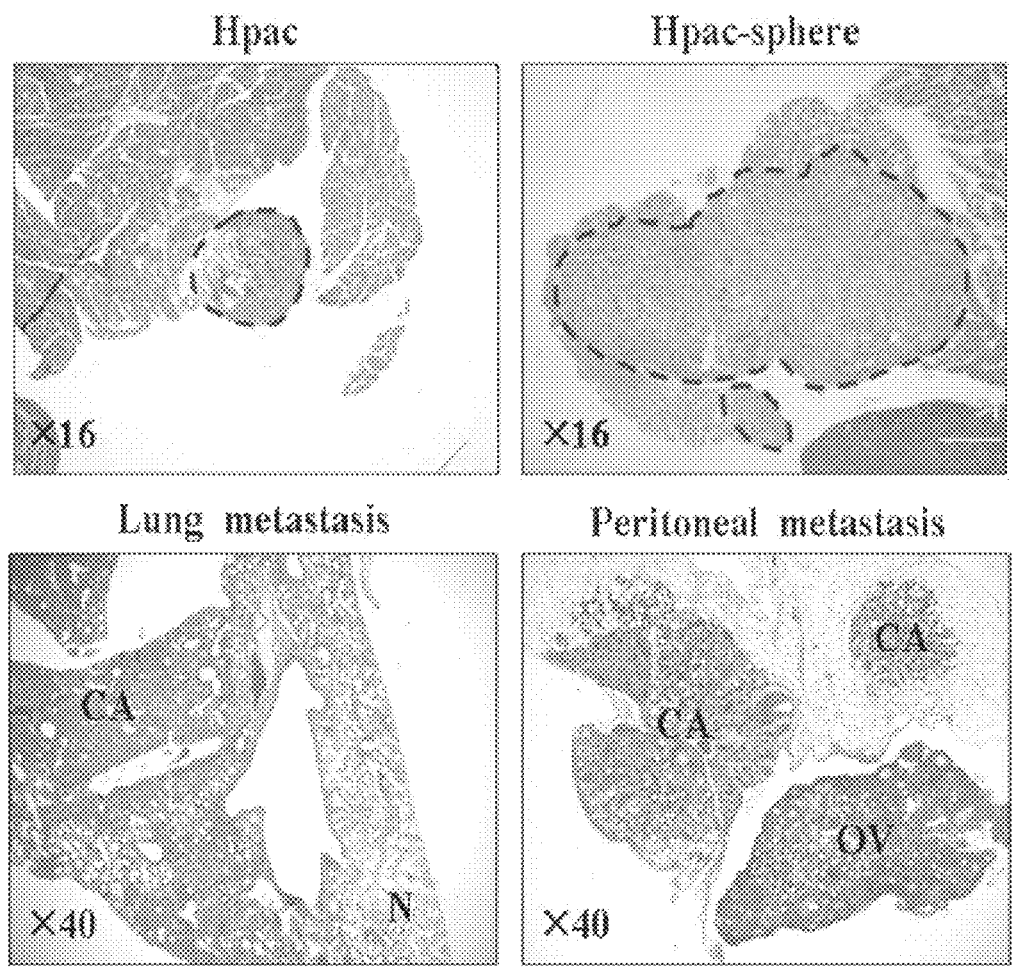
Figure 5C:
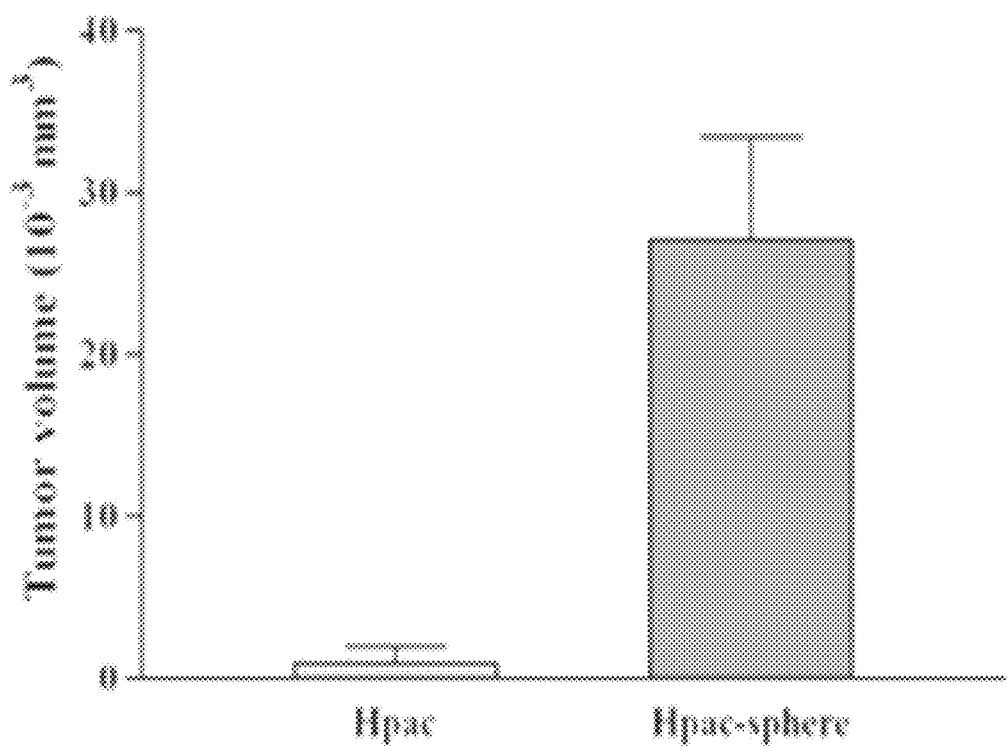

Hpac-spheres were in situ-implanted into pancreas of NOD/SCID mouse to validate tumorigenicity. The Hpac-spheres injected group was analyzed to be significantly higher than that for the adhesive Hpac cells injected group. In addition, pulmonary metastasis and peritoneal metastasis were observed in the Hpac-spheres injected group (FIGS. 5a-c).

Hpac-spheres express cancer stem cell-related genes and markers. It would be understood that pancreatic cancer stem cell-specific markers may be predicted by investigating profiles of proteins secreted from Hpac-spheres, based on these results showing enhanced tumorigenic potential (FIGS. 1-5c).

Analysis of Cancer Stem Cell-Related Secretory Proteins in Sphere Cells 587 paired spots were detected in Hpac-spheres, adhesive Hpac cells, Capan 1-spheres and adhesive Capan 1 cells. Among them, 55 spots which were increased more than two times in Hpac-spheres as compared to adhesive Hpac cells were detected.

41 spots in the 55 spots were subject to MALDI-TOF to identify pancreatic cancer stem cell-related secretory protein (Table 2).

TABLE 2

| Spot number | Fold change | GI number | Accession number | Protein name |
|---|---|---|---|---|
| 15378 | 4.1 | GI: 30268237 | CAD89908.1 | hypothetical protein |
| 15386 | 2.5 | GI: 41352061 | NP_055704.2 | metalloprotease 1 precursor |
| 15391 | 2.7 | GI: 20149594 | NP_031381.2 | heat shock 90 kDa protein 1, beta |
| 15413 | 2.7 | GI: 16507237 | NP_005338.1 | heat shock 70 kDa protein 5 |
| 15429 | 4.3 | GI: 145701028 | NP_001077415.1 | hypothetical protein LOC55471 isoform 3 |
| 15436 | 9.2 | GI: 56203587 | CAI21475.1 | 1-acylglycerol-3-phosphate O-acyltransferase 4 (AGPAT4) |
| 15470 | 2.3 | GI: 4504025 | NP_002055.1 | glutaredoxin |
| 15602 | 5.2 | GI: 39644662 | AAH09206.2 | HSP90AB1 protein |
| 15619 | 2.8 | GI: 21396487 | NP_653337.1 | hypothetical protein LOC55471 isoform 1 |
| 15665 | 2.3 | GI: 31543 | CAA27309.1 | unnamed protein product |
| 15680 | 2.2 | GI: 38014278 | AAH01678.2 | TUBB3 protein |
| 15687 | 2.3 | GI: 62414289 | NP_003371.2 | vimentin |
| 15737 | 4.3 | GI: 24308169 | NP_060009.1 | dynein, axonemal, heavy chain 3 |
| 15792 | 2.3 | GI: 4504025 | NP_002055.1 | glutaredoxin |
| 15805 | 2.0 | GI: 119586807 | EAW66403.1 | hCG2042304 |
| 15821 | 3.3 | GI: 34304594 | AAQ63403.1 | hypothetical protein FLJ10808 isoform |
| 15871 | 3.3 | GI: 998688 | AAB34148.1 | erythrocyte 26 S protease subunit 12 |
| 15882 | 6.2 | GI: 28839796 | AAH47896.1 | RPS6KA4 protein (MSK2) |
| 15890 | 2.1 | GI: 48257132 | AAH14372.2 | GLRX3 protein |
| 15977 | 3.8 | GI: 4502049 | NP_001619.1 | aldo-keto reductase family 1, member B1 |
| 15978 | 3.4 | GI: 4502049 | NP_001619.1 | aldo-keto reductase family 1 (AKR1) |
| 16000 | 2.3 | GI: 171848760 | 2PD5_A | Chain A, Human Aldose Reductase Mutant V47i |
| 16026 | 2.5 | GI: 8118090 | AAF72885.1 | formin 2-like protein |
| 16051 | 17.0 | GI: 21389577 | NP_653280.1 | hypothetical protein LOC146705 |
| 16087 | 4.4 | GI: 157168362 | NP_000261.2 | nucleoside phosphorylase |
| 16095 | 3.7 | GI: 4503143 | NP_001900.1 | cathepsin D preproprotein |
| 16139 | 2.1 | GI: 158261815 | BAF83085.1 | unnamed protein product |
| 16159 | 2.6 | GI: 47682755 | AAH70129.1 | TPI1 protein |
| 16193 | 2.5 | GI: 662841 | AAA62175.1 | heat shock protein 27 |
| 16246 | 2.2 | GI: 60593959 | 1X71_A | Chain A, Crystal Structure Of Siderocalin |
| 16268 | 2.1 | GI: 544759 | AAB29537.1 | biliverdin-IX beta reductase isozyme I |
| 16288 | 2.0 | GI: 14042653 | BAB55338.1 | unnamed protein product |
| 16337 | 2.0 | GI: 119588464 | EAW68058.1 | tetraspanin 18, isoform CRA_a |
| 16432 | 2.2 | GI: 158259341 | BAF85629.1 | unnamed protein product |
| 16528 | 2.5 | GI: 16549206 | BAB70777.1 | unnamed protein product |
| 16610 | 2.9 | GI: 178375 | AAB46377.1 | aldehyde dehydrogenase (ALDH) |
| 16625 | 5.6 | GI: 13489087 | NP_109591.1 | serine (or cysteine) proteinase inhibitor, clade B |
| 16629 | 9.4 | GI: 4558862 | AAD22767.1 | A-kinase anchoring protein AKAP350 |
| 16640 | 2.4 | GI: 21752882 | BAC04252.1 | unnamed protein product |

TABLE 2-continued

| Spot number | Fold change | GI number | Accession number | Protein name |
|---|---|---|---|---|
| 16643 | 5.3 | GI: 119568120 | EAW47735.1 | spectrin repeat containing, nuclear envelope 1 |
| 16650 | 2.3 | GI: 119617987 | EAW97581.1 | hCG2015069 |

Proteins including HSP90AB1, ALDH and vimentin which have been reported to be associated with cancer stem cell were identified. These results suggest that the secretory proteins described in Table 1 have potential to be pancreatic cancer stem cell-related secretory proteins.

Expression Verification of Pancreatic Cancer Stem Cell-Related Secretory Proteins in Sphere Cell Media Through Western Blot In order to verify expressions of pancreatic cancer stem cell-related secretory proteins identified by MALDI-TOF analysis, the media of adhesive Hpac cells, Hpac-spheres, adhesive Capan 1 cells and Capan 1-spheres were subject to western blot. It was verified that 5 secretory proteins including GLRX3 were increased in Hpac-spheres and Capan 1-spheres.

Verification on Expressions of mRNA and Protein of GLRX3 in Pancreatic Cancer Cell Lines To verify GLRX3 expression, mRNA and protein were extracted in eight pancreatic cancer cell lines (AsPC-1, BxPC-3, Capan-1, Capan-2, Cfpac-1, HPAC, Panc-1 and Miapaca-2) and HPDE (Human Pancreatic Ductal Epithelial cell). As a result, it was determined that both of mRNA and protein of GLRX3 were over-expressed in eight pancreatic cancer cell lines. In addition, it was found that pancreatic cancer cell lines except for Hpac extracellularly secreted GLRX3 protein through western blot in the media (FIG. 7).

Figure 8:
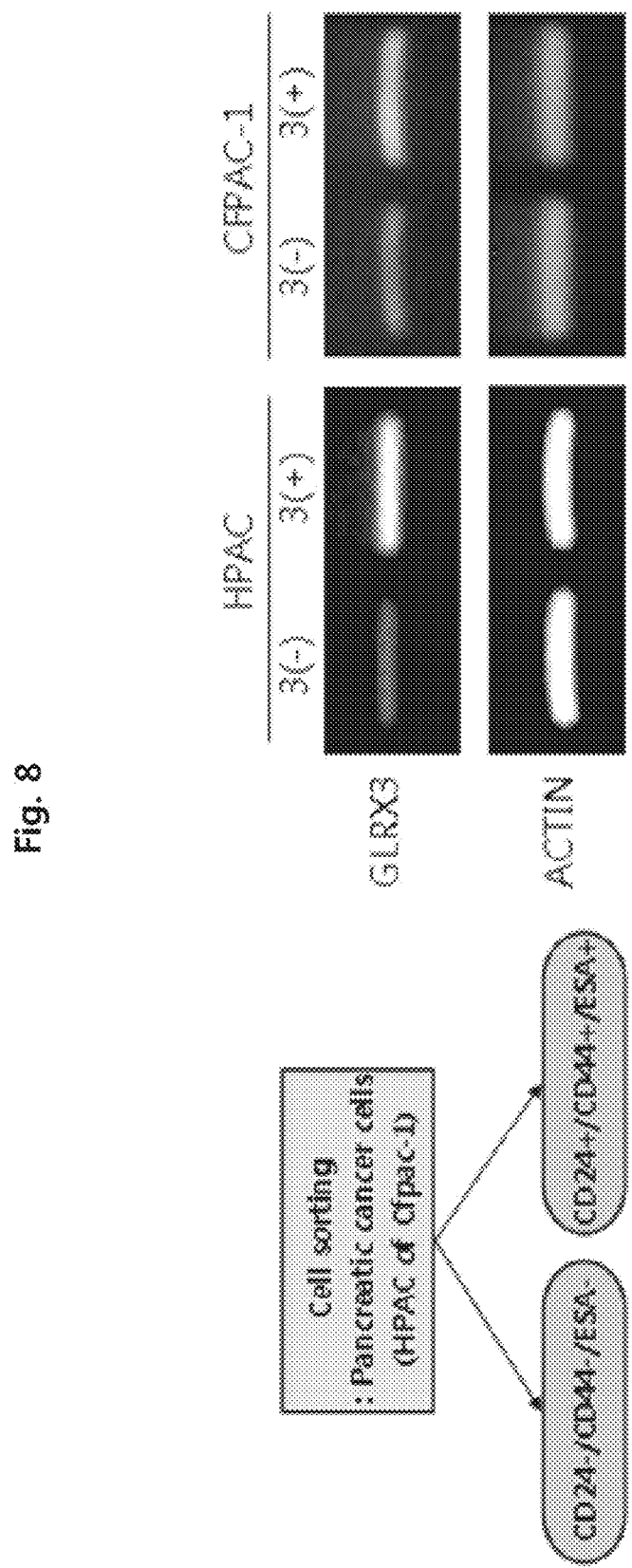
FIG. 8 represents results of verifications on expressions of GLRX3 in cells expressing 3 types of markers (CD24+/CD44+/ESA+) and cells non-expressing 3 types of markers (CD24−/CD44−/ESA−).

Verification on Over-Expression of GLRX3 in the Cell Fraction Having Properties of Pancreatic Cancer Stem Cells Hpac was fluorescence-stained by cancer stem cell marker CD24, CD44 and ESA. Then, cells expressing 3 types of markers (CD24+/CD44+/ESA+) and cells non-expressing 3 types of markers (CD24−/CD44−/ESA−) were fractionized. As a result, it was verified that GLRX3 in cells expressing 3 types of markers (CD24+/CD44+/ESA+) were over-expressed than that of cells non-expressing 3 types of markers (CD24−/CD44−/ESA−). The same results were shown in CFPAC-1 (FIG. 8).

Figure 9:
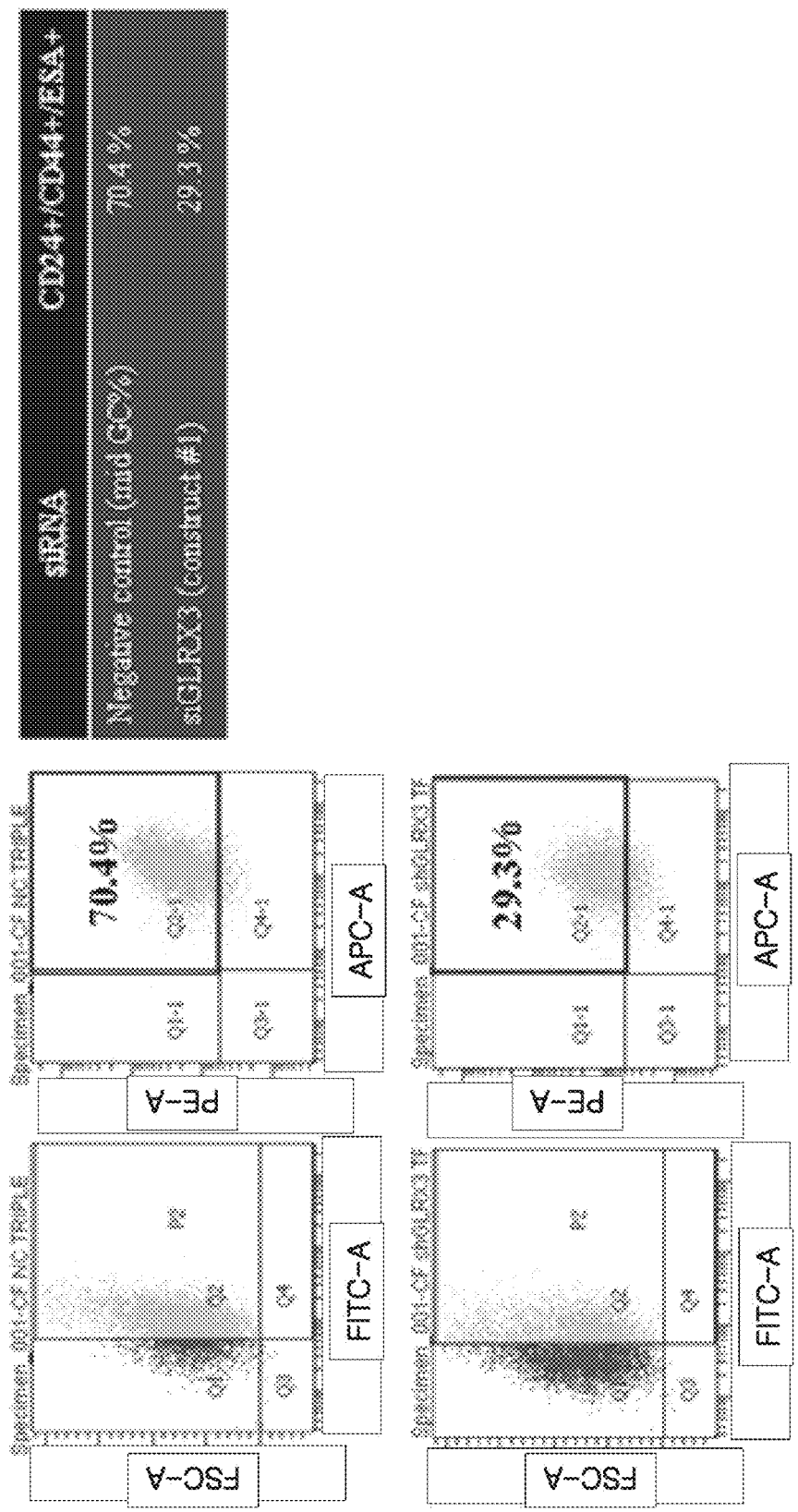
FIG. 9 represents results of verifications on expression changes of 3 markers (CD24+/CD44+/ESA+) in inhibitory effects of GLRX3 siRNA and control siRNA

In addition, the fractions of cancer stem cells were changed by inhibition of GLRX3 expression. It was verified that fraction of CD24+/CD44+/ESA+ was decreased to 29.3% from 70.4% where siRNA to GLRX3 were treated (FIG. 9).

GLRX3 Knock-Down Cell Line Establishment and Characterization

Figure 10:
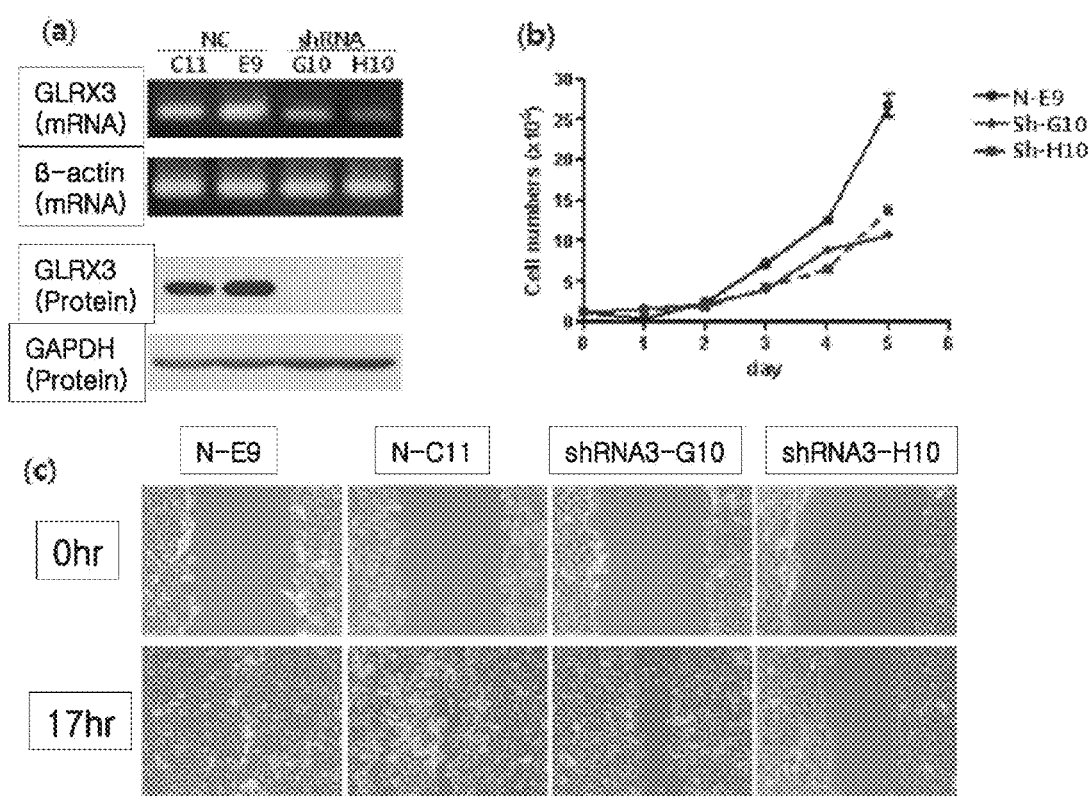

To verify inhibitory effects of GLRX3 expression, shRNA to GLRX3 and control shRNA were prepared. Hpac cell line was transfected with the shRNAs to establish GLRX3 knock-down (k/d) cell line. Expressions of mRNA and protein of GLRX3 in the established GLRX3 knock-down (k/d) cell line were significantly reduced (FIG. 10a). In order to verify cancer-related characteristic changes of the GLRX3 k/d, two clones of the GLRX3 k/d cell line and two clones of the control were selected. It was determined that the cell proliferation rate in the GLRX3 k/d cell line was decreased as compared to the control (FIG. 10b), and a result of wound-healing assay, cell migration activity in the GLRX3 k/d cell line was decreased as compared to the control (FIG. 10c).

Figure 11:
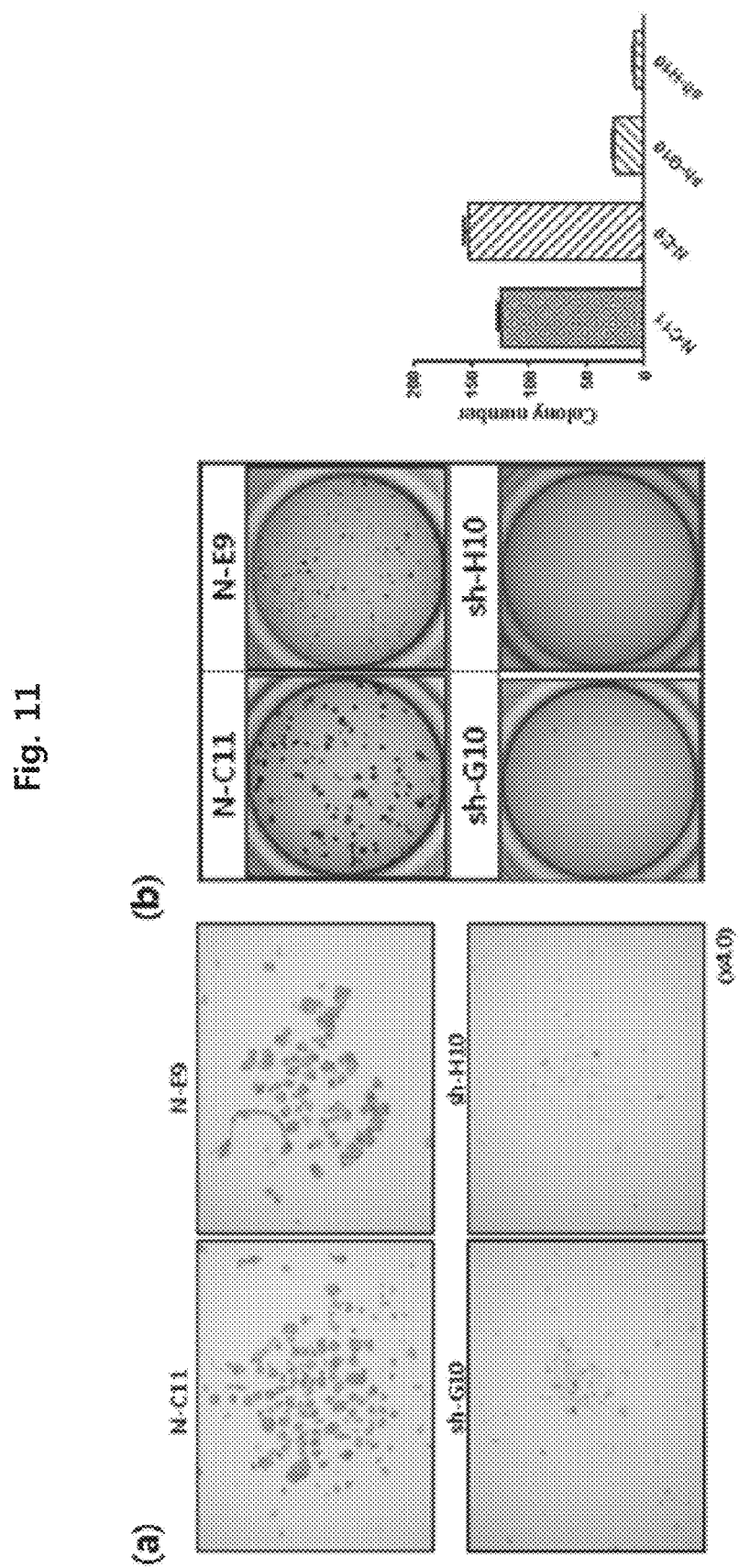
FIGS. 11a-b represent results of verifications on cancer stem cell-related characteristic changes in GLRX3 knock-down cell line.

Analysis of Cancer Stem Cell-Related Characteristic Changes in GLRX3 Knock-Down Cell Line As GLRX3 were revealed as cancer stem cell-related protein, cancer stem cell-related characteristic changes induced by the GLRX3 k/d were investigated. First, ability to form spheres of the GLRX3 k/d cell line and the control cell line was verified (FIG. 11a). As a result, the spheres were not formed in the GLRX3 k/d cell line, whereas the spheres were formed in the control cell line. These results are shown as the same results in the sphere culture that GLRX3 expression was increased. In addition, as a result of clonogenic assay showing viability and proliferation, the GLRX3 k/d cell line formed fewer colonies than the control cell line (FIG. 11b).

In these results, GLRX3 showed not only possibility as oncogenic markers related to pancreatic cancer stem cells, but also as targets for pancreatic cancer therapeutic agents based on inhibitory effects to various cancer-related characteristic induced by GLRX3 inhibition.

Figure 12:
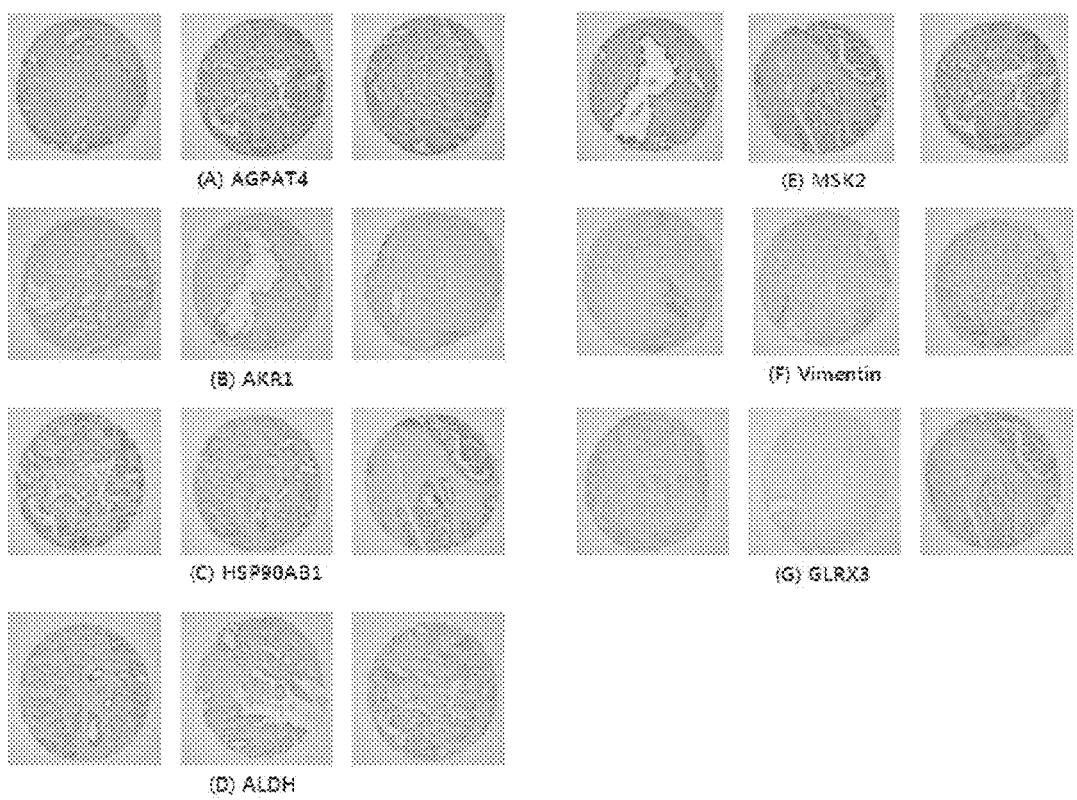
FIG. 12 is images showing verifications of pancreatic cancer stem cell-related secretory proteins in human pancreatic cancer tissue microarray through immunohistochemistry. It could be appreciated that all 7 pancreatic cancer stem cell-related secretory proteins including AGPAT4 and GLRX3 were strongly expressed in pancreatic cancer tissue.

Expression Verification of Pancreatic Cancer Stem Cell-Related Secretory Proteins In Human Pancreatic Cancer Tissue AGPAT4 was expressed in TMA slides of total 29 cases, and classified as "++" (15 cases) and "+++" (14 cases) in 100% of pancreatic cancer patient tissues (panel (A) in FIG. 12).

AKR1B1 was expressed in TMA slides of total 27 cases, and classified as "−" (10 cases), "+" (15 cases) and "++" (2 cases) in 62.9% of pancreatic cancer patient tissues (panel (B) in FIG. 12).

HSP90 was expressed in TMA slides of total 28 cases, and classified as "+" (1 case), "++" (19 cases) and "+++" (8 cases) in 100% of pancreatic cancer patient tissues (panel (C) in FIG. 12).

ALDH was expressed in TMA slides of total 26 cases, and classified as "−" (4 cases), "+" (8 cases), "++" (7 cases) and "+++" (7 cases) in 84.6% of pancreatic cancer patient tissues (panel (D) in FIG. 12).

MSK2 was expressed in TMA slides of total 27 cases, and classified as "−" (1 case), "+" (5 cases), "++" (8 cases) and "+++" (13 cases) in 96.2% of pancreatic cancer patient tissues (panel (E) in FIG. 12).

Vimentin was mainly stained in extracellular interstitium. Although a lot of the stained cells formed tubular structure, they were thought to be non-cancer cells. Vimentin was hardly stained in cytoplasm of cancer cells. Vimentin was focal-stained in 1 case among 28 cases of pancreatic cancer tissues (panel (F) in FIG. 12).

GLRX3 was expressed in TMA slides of total 25 cases, and classified as "−" (11 cases), "+" (11 cases) and "++" (4 cases) in 57.6% of pancreatic cancer patient tissues (panel (G) in FIG. 12).

Figure 13:
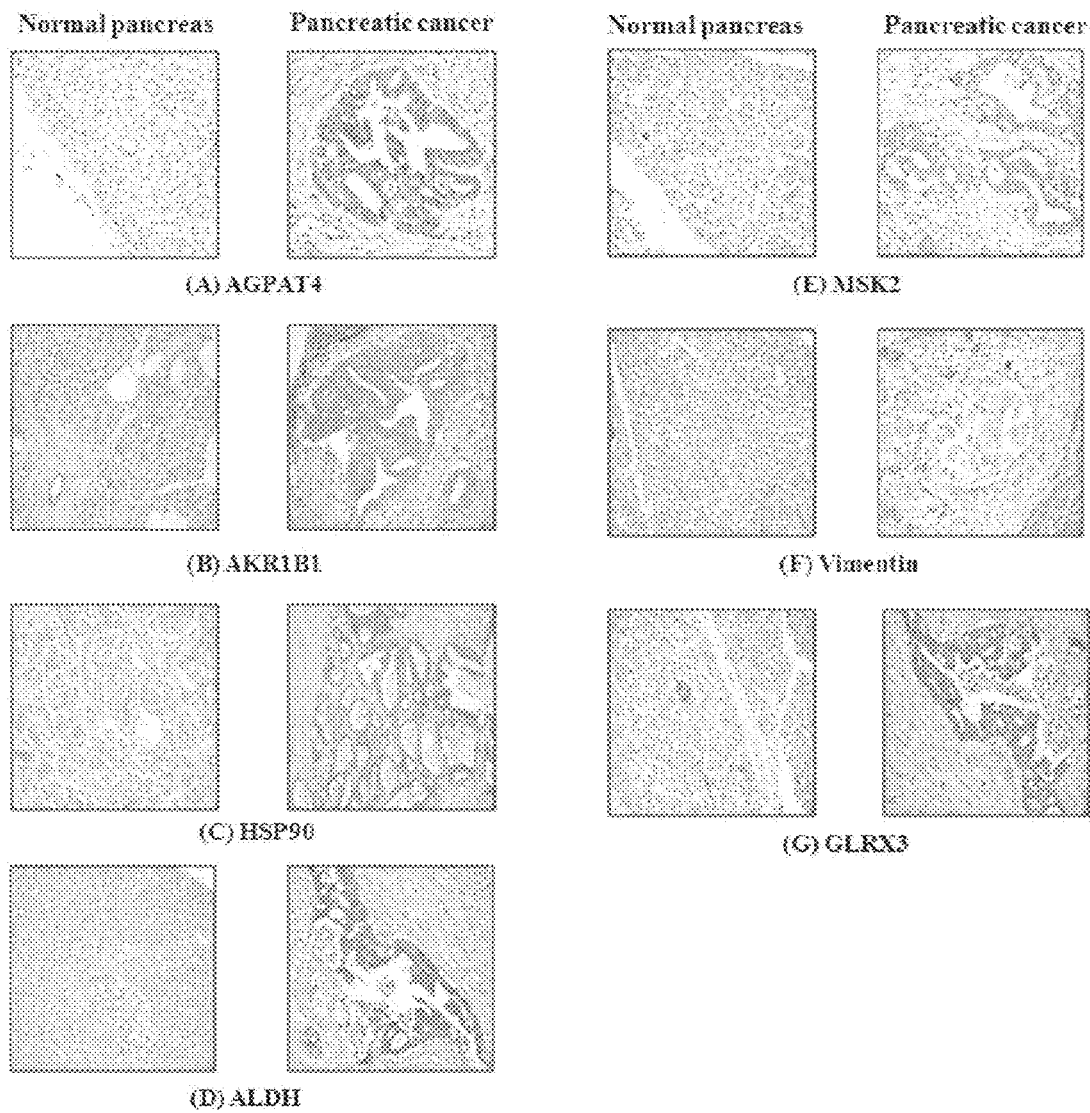
FIG. 13 is images showing expression verifications of 7 pancreatic cancer stem cell-related secretory proteins including AGPAT4 and GLRX3 in human normal and pancreatic cancer tissue. It could be appreciated that all 7 pancreatic cancer stem cell-related secretory proteins were strongly expressed in pancreatic cancer tissue as compared to normal pancreatic tissue.

Paraffin sections in surgical tissue of pancreatic cancer patients were stained by immunohistochemistry to verify expressions of pancreatic cancer stem cell-related secretory proteins. It could be appreciated that all 7 pancreatic cancer stem cell-related secretory proteins including GLRX3 (developed by the present invention), HSP90AB1, ALDH and vimentin which have been already reported to be associated with cancer stem cell were strongly expressed in pancreatic cancer tissue as compared to normal pancreatic tissue (panel (A)-(G) in FIG. 13).

Expression Verification of Secretory Proteins Developed in Sera of Human Normal, Chronic Pancreatitis and Pancreatic Cancer Patients As the absence of commercial ELISA kit for the developed secretory proteins, some proteins were subject to western blot to verify expressions.

Figure 14A:
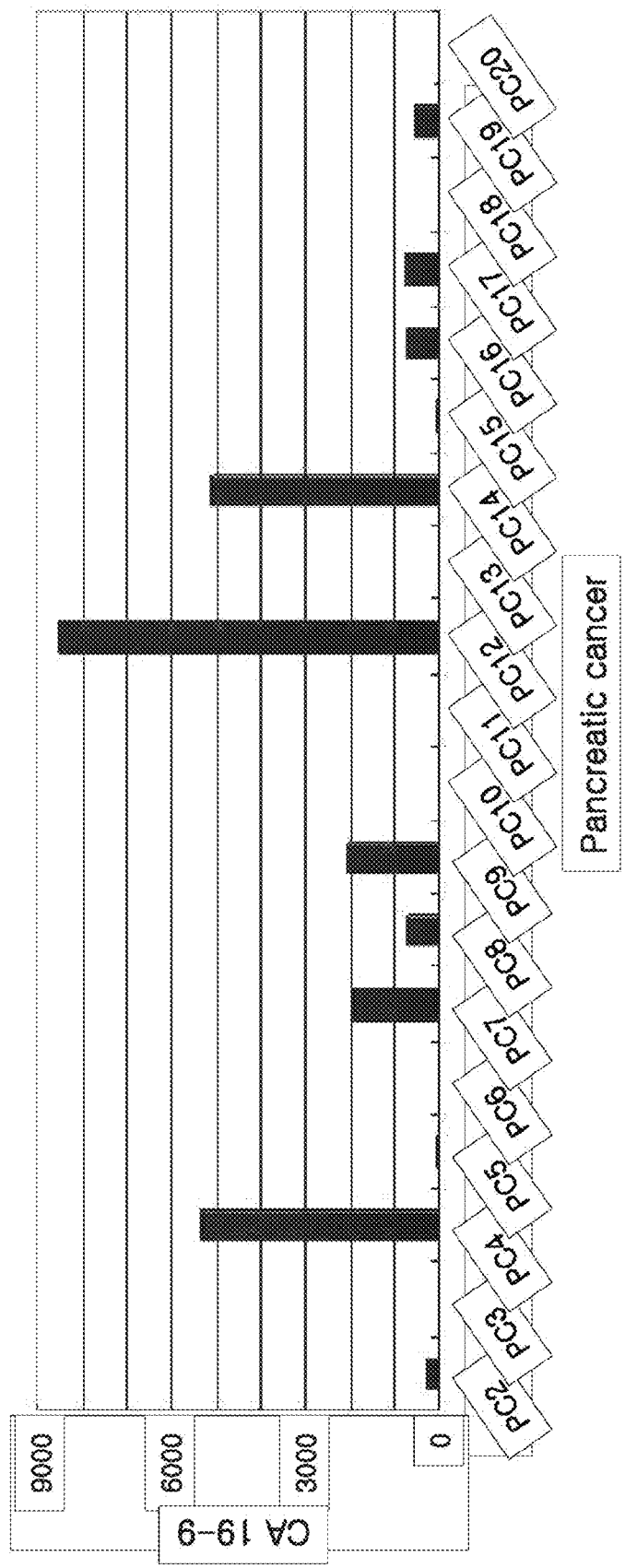
FIG. 14a represents results of expression verifications of a conventional pancreatic cancer marker CA19-9 in sera of pancreatic cancer patients.
Figure 14B:
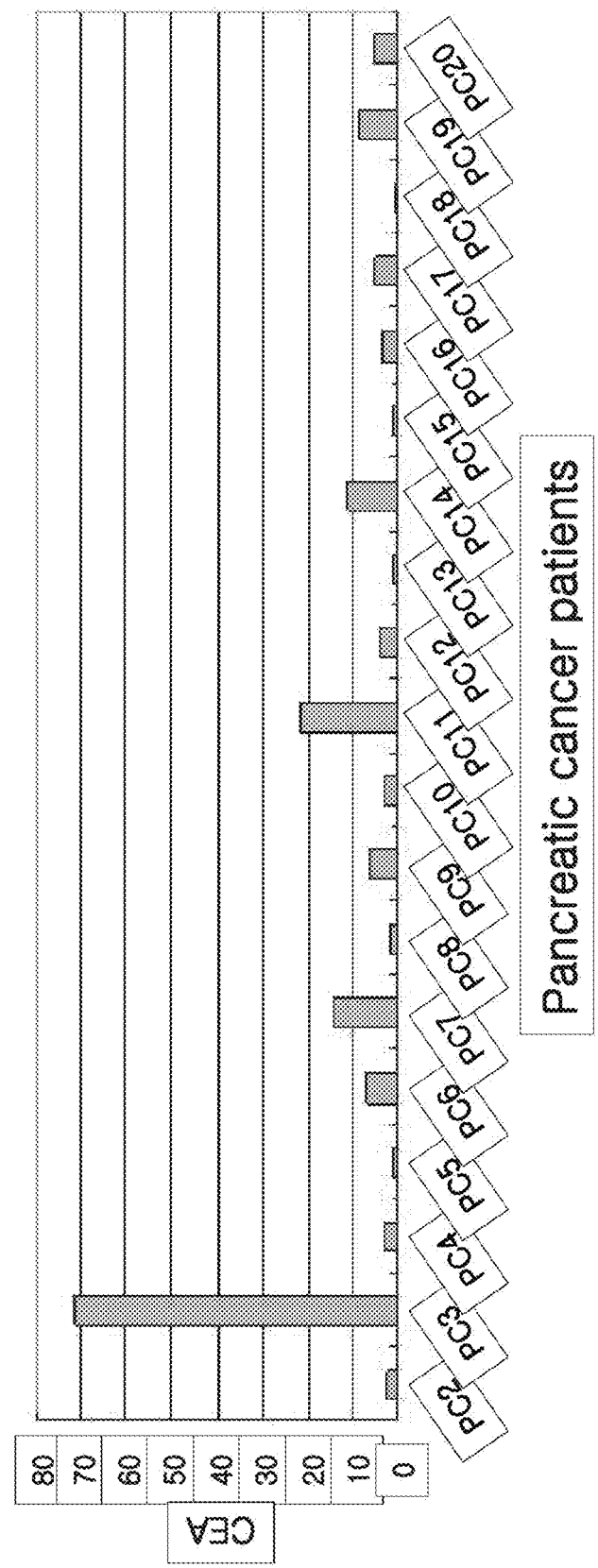
FIG. 14b represents results of expression verifications of a conventional pancreatic cancer marker CEA in sera of pancreatic cancer patients. It could be appreciated that there was clearly differences of expressions between conventional pancreatic cancer markers CA 19-9 and CEA according to patients even thought the markers CA19-9 and CEA are currently being used for diagnostic markers in pancreatic cancer.
Figure 15A:
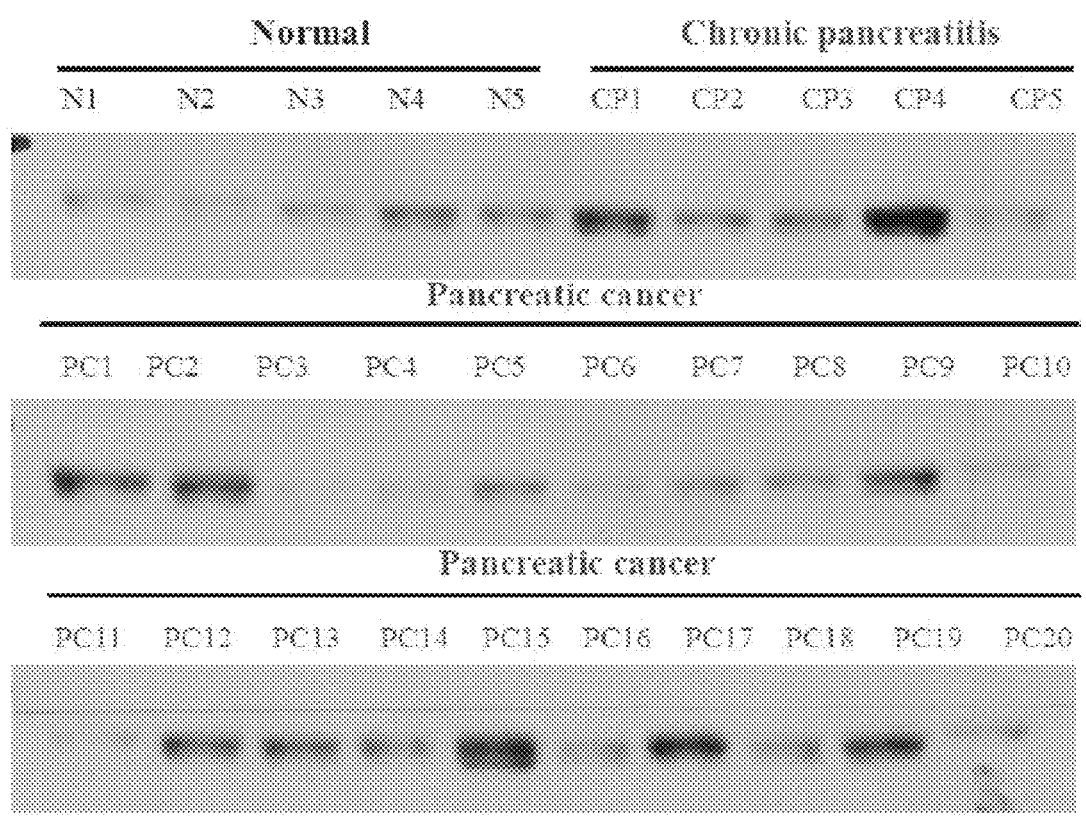
FIGS. 15a-b represent results of expression verifications of MSK2 protein through western blot after detections of sera in normal, chronic pancreatitis patient and pancreatic cancer patient using MARS (Multiple affinity removal column system).
Figure 15B:
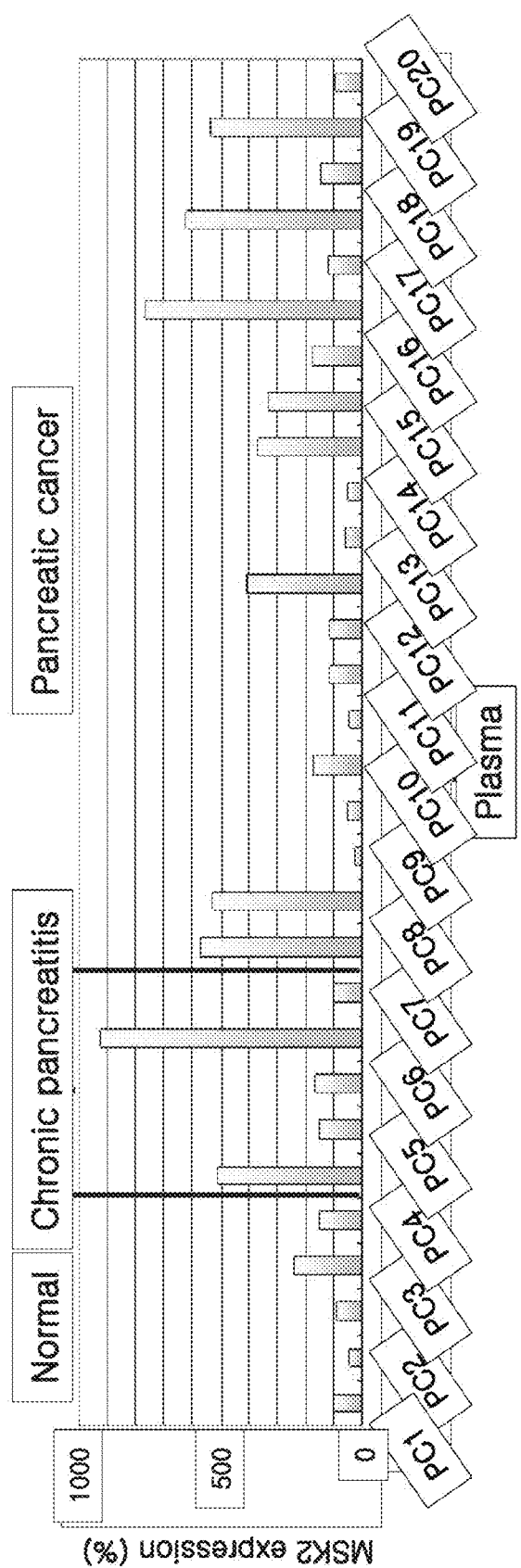
Figure 16A:
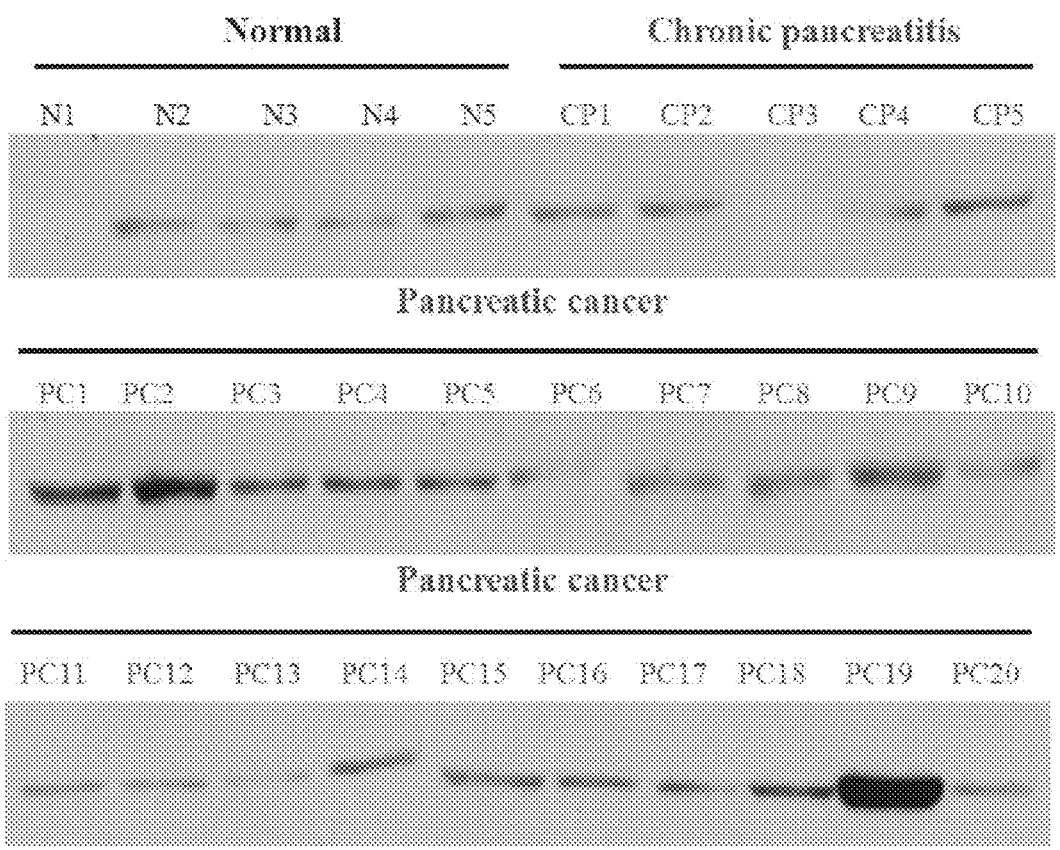
FIGS. 16a-b represent results of expression verifications of vimentin protein through western blot after detection of sera in normal, chronic pancreatitis patient and pancreatic cancer patient using MARS.
Figure 16B:
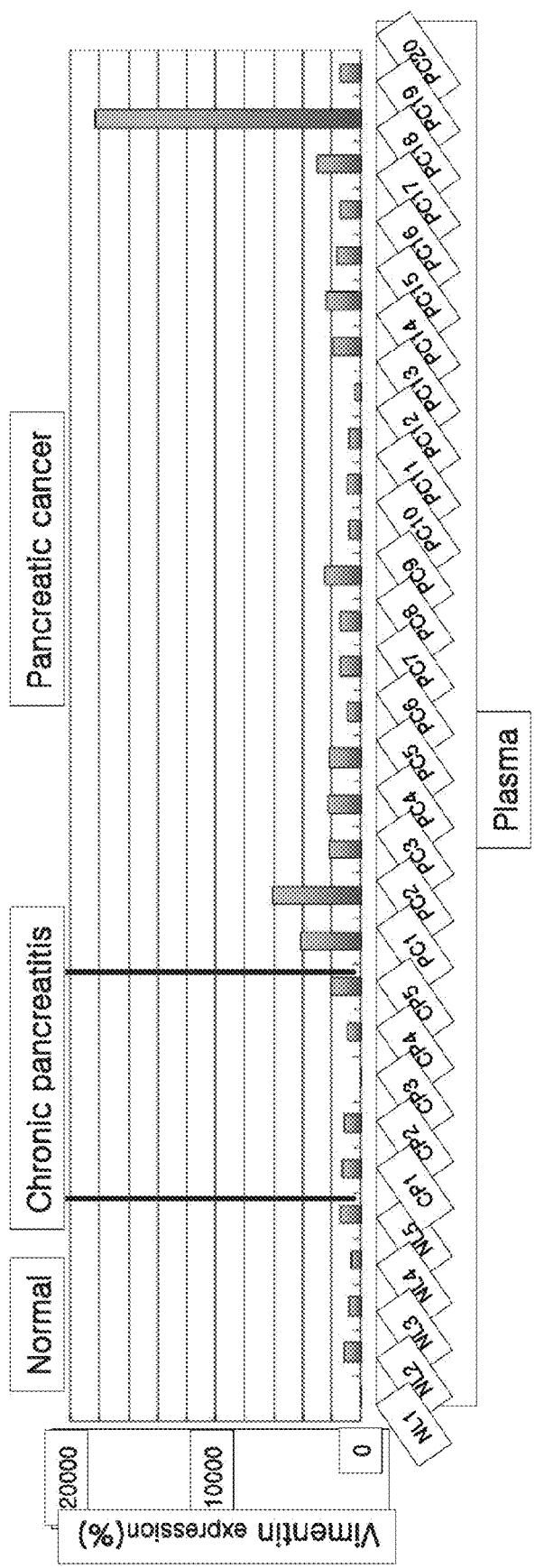
Figure 17A:
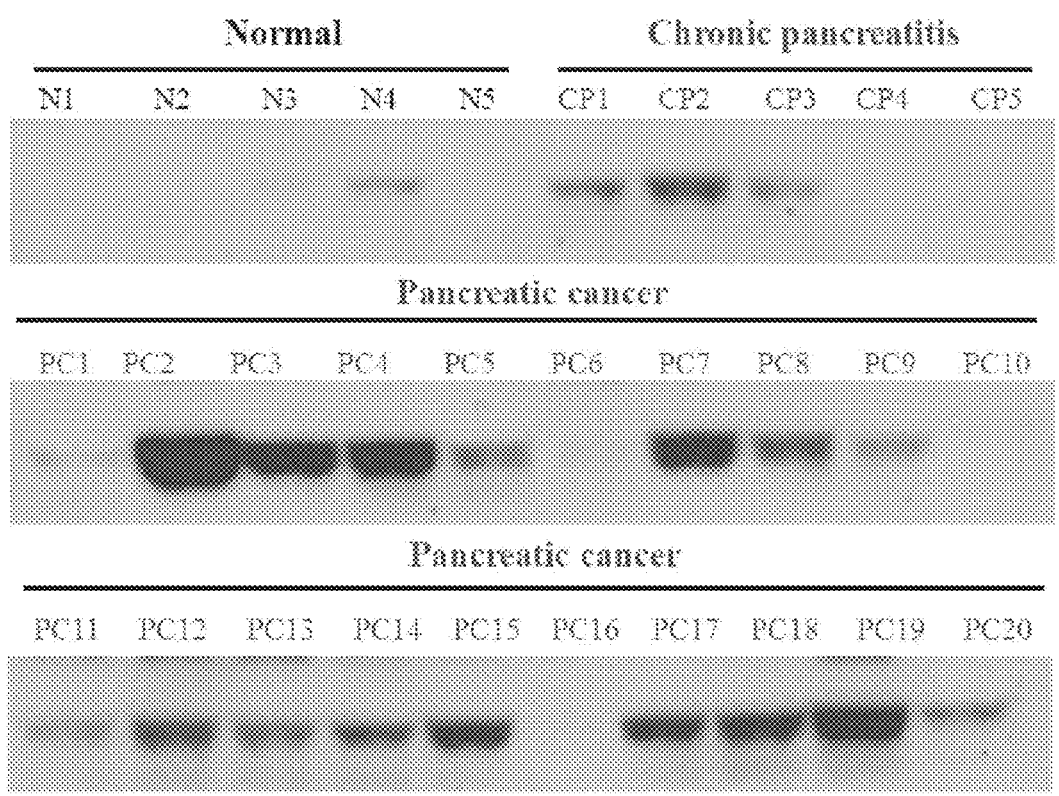
FIGS. 17a-b represent results of expression verifications of ALDH protein through western blot after detection of sera in normal, chronic pancreatitis patient and pancreatic cancer patient using MARS.
Figure 17B:
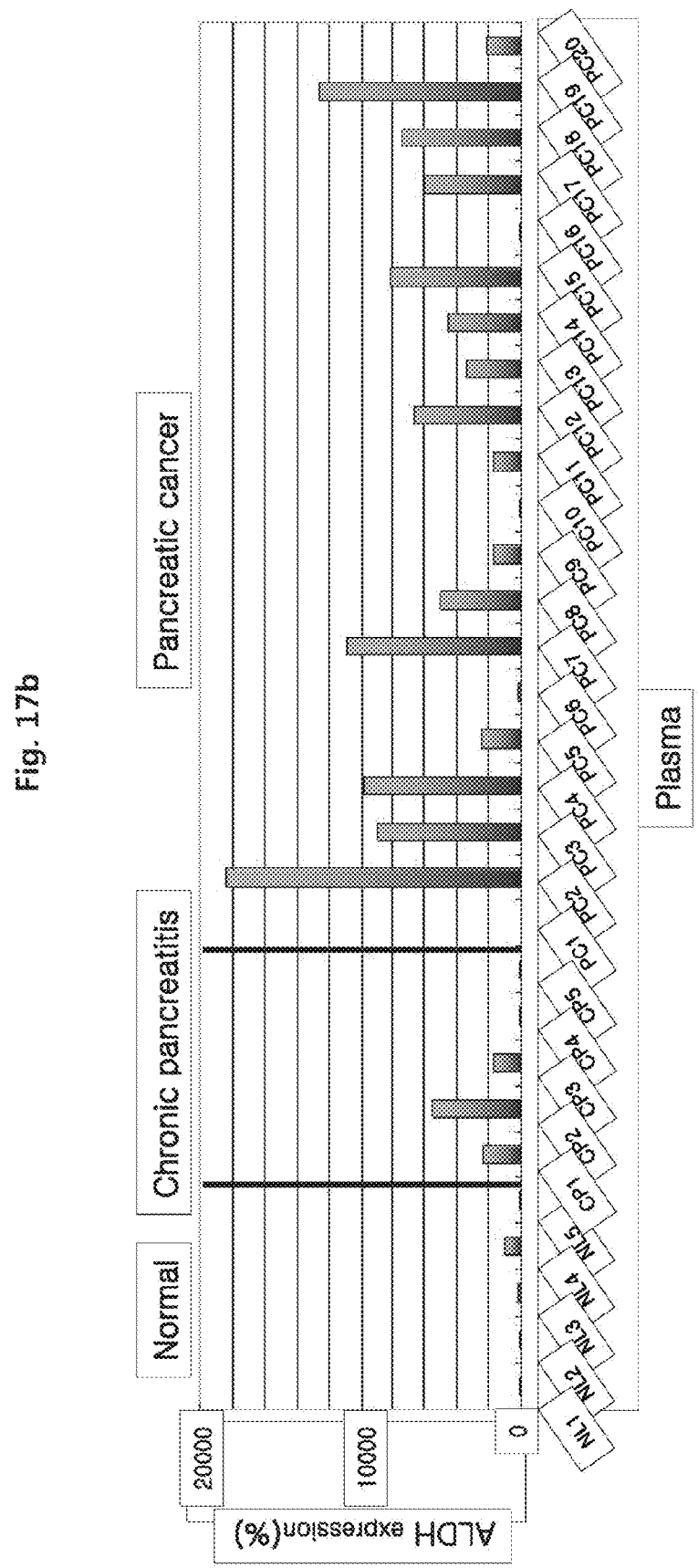

To verify expressions of pancreatic cancer stem cell-related secretory proteins developed in sera of human normal, chronic pancreatitis and pancreatic cancer patients, normal serum 5 cases, chronic pancreatitis serum 5 cases and pancreatic cancer serum 20 cases were selected. To compare pancreatic cancer stem cell-related secretory proteins developed in the present invention with conventional pancreatic cancer markers (CA 19-9 and CEA), levels of CA 19-9 and CEA in serum of the selected pancreatic cancer patients (PC2-PC10) were shown in FIGS. 14a-b.

Prior to verification of the developed secretory protein expressions through western blot, 6 principal proteins (albumin, transferrin, IgG, IgA, haptoglobin and anti-trypsin) in total 30 cases of the sera were removed using MARS (Multiple affinity removal column system), and then, the sera were concentrated using amicon ultra centifugal filter device with 3 kDa molecular-mass cut off (MWCO) to quantify proteins. An equal concentration of the proteins was used in western blot.

Secretory proteins vimentin and ALDH which have been well-known to be associated with cancer stem cells showed results that they were over-expressed in pancreatic cancer patient serum as compared to normal and chronic pancreatitis patient sera. In addition, whereas GLRX3 as the developed pancreatic cancer stem cell secretory protein was very low-expressed in normal serum, GLRX3 was high-expressed in more than 50% of pancreatic cancer patient serum as compared to normal and chronic pancreatitis patient sera (FIGS. 15a-18b).

Expression Verification of GLRX3 in Pancreatic Cancer Patient Blood

Figure 19:
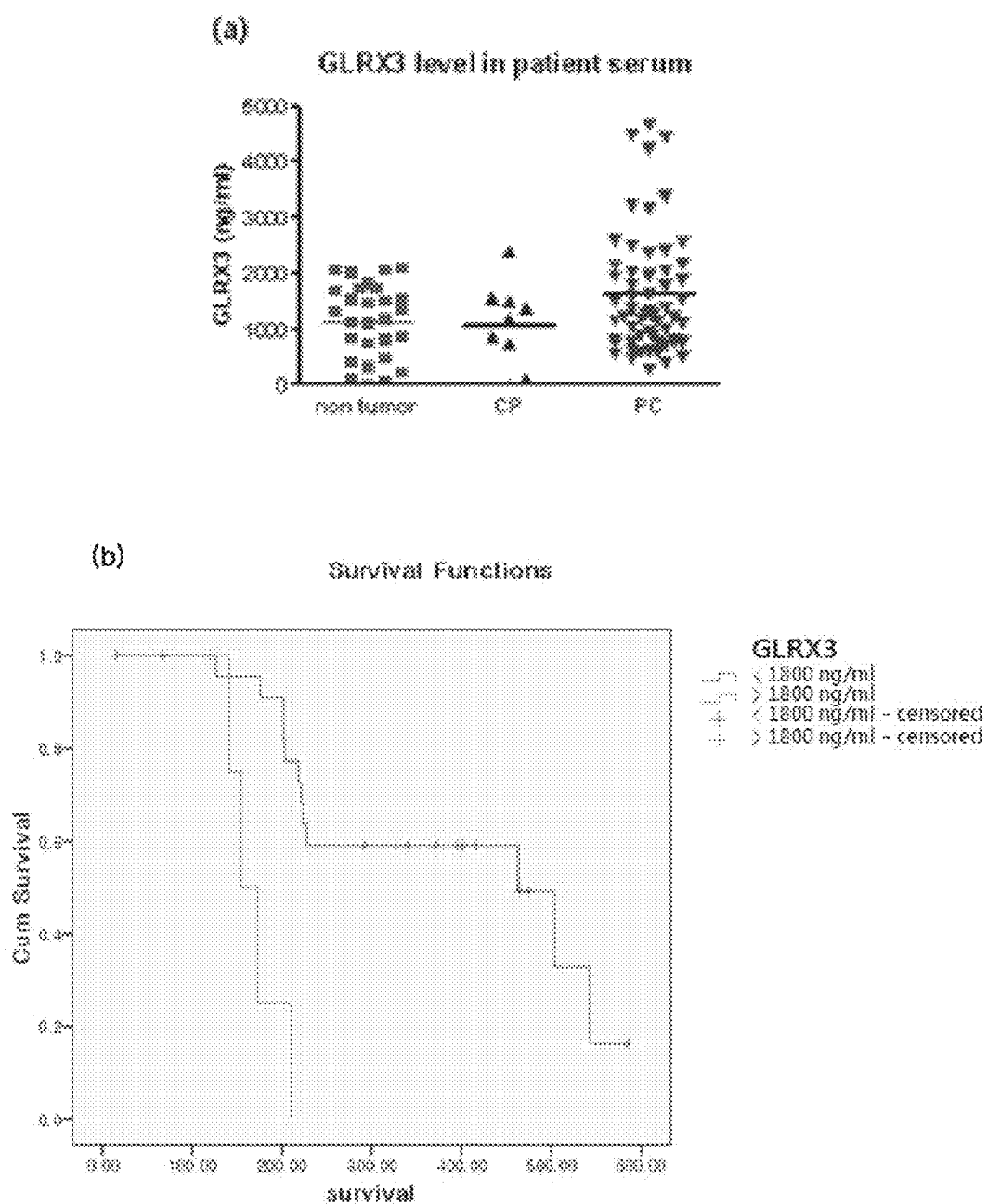
FIGS. 19a-b represent results of expression verifications of GLRX3 protein through ELISA in pancreatic cancer patient serum.

In order to verify expressions of GLRX3 in clinical patients, ELISA was performed using ELISA kit (USCN GLRX3 ELISA kit). As a result of ELISA in normal control 28 cases, chronic pancreatitis patients 9 cases and pancreatic cancer patients 57 cases, it was determined that GLRX3 was high-expressed in pancreatic cancer patient blood (FIG. 19a). Particularly, there were differences of survival periods according to GLRX3 level that survival periods of patients showing less than 1800 ng/mL of GLRX3 level were 463 days, whereas survival periods of patients showing more than 1800 ng/mL of GLRX3 level were 155 days (FIG. 19b).

Discussion

Cancer stem cells are cancer cells that possess the abilities to maintain and regenerate cancer tissues like normal stem cells. Cancer stem cells are not only thought to be involved in oncogenesis, but also have been reported that they profoundly influence cancer recurrence, metastasis or resistance to chemotherapy by involving regeneration of cancer cells after anticancer therapies (BB Zhou et al. *Nat Rev Drug Discov.,* 8:806-823 (2009)). Cancer stem cells are a rare population of heterogenous cancer cells and they have been known as tumor initiating cells which have ability to form tumor. Where these cells are suspension-cultured in vitro, they form spheres. It has been reported that the cells obtained from sphere-culture have stronger ability to form tumor than that of the original cell line (A. Dubrovska et al. *Proc Natl Acad Sci USA.,* 106:268-273 (2009)). In addition, genes and proteins related to several cancers and cancer stem cell have been known to be strongly expressed in these cells than that of the original cell line.

In the present invention, it was verified that spheres formed from pancreatic cancer cell lines have the capacity to self-renewal by generating sub-spheres, and they have aberrant activation of stem cell-related signaling pathways such as Notch, Hedgehog, and Wnt (T. Reya et al. *Nature,* 414:105-111 (2001)). In addition, it could be determined that early embryonic development related genes such as Oct4, nanog and stat3 which represent multipotency of stem cell were over-expressed. Besides, PTEN which plays a pivotal rule in cancer survival and maintenance were over-expressed, of which showed the results consistent with previous reports related to stem cells (J. Zhou et al. *Proc Natl Acad Sci USA.,* 104:16158-16163 (2007)). As a result of Fluorescence-Activated Cell Sorting, it could be determined that well-known cancer stem cell markers CD44, PROM2, EphA2, CD130 and CD271 were over-expressed in adhesive Hpac cells and Hpac-spheres.

Based on these results, the present inventors have carried out proteomics analysis in order to connect roles of cancer stem cells recognized as the early symptoms of oncogenesis, and to identify and verify proteins secreted in sphere-culture, whereby proteins specifically secreted in pancreatic cancer patients were validated.

As a result of proteomics, the secretory proteins HSP90, vimentin, HSP27, ALDH, AGPAT4, AKR1B1, MSK2 and GLRX3 were identified. In pancreatic cancer tissues, these secretory proteins expressions were significantly increased as compared to normal tissues. Moreover, in pancreatic cancer patient sera, these secretory proteins expressions were significantly increased as compared to normal tissues. Although proteins were subject to western blot to verify expressions in serum due to the absence of commercial ELISA kit for the developed secretory proteins, it could be validated that expressions of the present secretory proteins were increased in pancreatic cancer patient sera.

Particularly, GLRX3 expression was increased in pancreatic cancer patient serum, and survival period of pancreatic cancer patients with high-expression of GLRX3 was relatively lower than that of pancreatic cancer patients with low-expression of GLRX3. In addition, where GLRX3 expression was inhibited, various cancer- and caner stem cell-related characteristics were decreased. Based on these results, GLRX3 were validated that it may be used to targets for diagnosing or treating as well as markers for prognosing pancreatic cancer.

In addition, many proteins were together identified as follows: HSP90 reported as therapeutic target for various cancers (L. Whitesell and S. L. Lindquist, *Nat Rev Cancer,* 5: 761-772 (2005)); vimentin as a marker for epithelial to Mesenchymal transition associated with cancer stem cells (J M. Lee et al. *J Cell Biol.,* 172:973-981 (2006); PB. Gupta et al. *Cell.,* 138:645-659 (2009)); HSP27 associated with chemotherapy-resistant as characteristic of cancer stem cells (S. Oesterreich et al. *Cancer Res.,* 53:4443-4448 (1993)); and ALDH recently emerging as a cancer stem cell marker (C. Jauffret et al. *Clin Cancer Res.,* 16:45-55 (2010)). This result suggests that the secretory proteins developed in the present invention have possibility to be cancer stem cell-related secretory proteins.

Pancreatic cancer is one of the most deadly human tumors with 1-4% of 5 year survival rate and 5 months of median survival time, and it has an extremely poor prognosis. Since 80-90% of patients are diagnosed at an advanced stage of being not possible to cure by curative resection, it leads to a poor clinical outcome. In addition, anticancer therapies mainly depend on chemotherapies. Therefore, development for the early diagnosis method in pancreatic cancer is urgently needed than any other human cancers.

To date, therapeutic effects of several anticancer agents including 5-fluorouracil, gemcitabine and tarceva known to be effective in pancreatic cancer are very disappointing, and there is only approximately 15% of the response rate to chemotherapy. These facts suggest that developments for the early diagnosis method and therapeutic method to pancreatic cancer in more effective manner are urgently needed.

Accordingly, it would be understood that improved diagnosis methods using cancer stem cells may be proposed by development of early diagnosis of cancer and combinations with the conventional markers, given that successive studies on cancer stem cell-related secretory proteins developed in the present invention have been done. Further, the present invention provides novel therapeutic targets to cancers. Taken together, the present invention may provide underlying principles for cancer diagnosis and therapeutics using cancer stem cells.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

REFERENCES

1. B B Zhou, et al. Tumour-initiating cells: challenges and opportunities for anticancer drug discovery. *Nat Rev Drug Discov.* 8:806-823 (2009).
2. A. Dubrovska, et al., The role of PTEN/Akt/PI3K signaling in the maintenance and viability of prostate cancer stem-like cell populations. *Proc Natl Acad Sci USA.* 106:268-273 (2009).
3. M M Ho, et al., Side population in human lung cancer cell lines and tumors is enriched with stem-like cancer cells. *Cancer Res.* 67:4827-4833 (2007).
4. T Reya, et al., Stem cells, cancer, and cancer stem cells. *Nature.* 414: 105-111 (2001).
5. J Zhou, et al., Activation of the PTEN/mTOR/STAT3 pathway in breast cancer stem-like cells is required for viability and maintenance. *Proc Natl Acad Sci USA.* 104:16158-16163 (2007).
6. S V Shmelkov, et al., CD133 expression is not restricted to stem cells, and both CD133$^+$ and CD133$^-$ metastatic pancreatic cancer cells initiate tumors. *J Clin Invest.* 118:2111-2120 (2008).
7. L. Whitesell and S. L. Lindquist., HSP90 and The chaperoning of cancer. Nat Rev Cancer, 5:761-772 (2005).
8. J M. Lee, et al., The epithelial-.mesenchymal transition: new insights in signaling, development, and disease. *J Cell Biol.* 172:973-981 (2006).
9. PB. Gupta, et al., Identification of Selective Inhibitors of Cancer Stem Cells by High-Throughput Screening. *Cell.* 138: 645-659 (2009).
10. S. Oesterreich, et al., The small heat shock protein hsp27 is correlated with growth and drug resistance in human breast cancer cell lines. *Cancer Res.* 53:4443-4448 (1993).
11. C. Jauffret, et al., Aldehyde Dehydrogenase 1-positive cancer stem cells mediate metastasis and poor clinical outcome in inflammatory breast cancer. *Clin Cancer Res.* 16:45-55 (2010).
12. Na K, Lee E Y, Lee H J, et al. Human plasma carboxylesterase 1, a novel serologic biomarker candidate for hepatocellular carcinoma. *Proteomics* 9:3989-3999 (2009).

What is claimed is:

1. A method for treating GLRX3 (Glutaredoxin-3)-expressing pancreatic cancer in a mammalian subject in need thereof comprising, administering to the mammalian subject a therapeutically effective amount of an inhibitor against the GLRX3 (Glutaredoxin-3) activity or expression.

* * * * *

SEQUENCE LISTING

```
<160> NUMBER OF SEQ ID NOS: 4

<210> SEQ ID NO 1
<211> LENGTH: 1008
<212> TYPE: DNA
<213> ORGANISM: Homo sapiens

<400> SEQUENCE: 1
atggcggcgg gggcggctga ggcagctgta gcggccgtgg aggaggtcgg ctcagccggg      60
cagtttgagg agctgctgcg cctcaaagcc aagtccctcc ttgtggtcca tttctgggca     120
ccatgggctc cacagtgtgc acagatgaac gaagttatgg cagagttagc taaagaactc     180
cctcaagttt catttgtgaa gttggaagct gaaggtgttc ctgaagtatc tgaaaaatat     240
gaaattagct ctgttccac ttttctgttt ttcaagaatt ctcagaaaat cgaccgatta     300
gatggtgcac atgccccaga gttgaccaaa aaagttcagc gacatgcatc tagtggctcc     360
ttcctaccca gcgctaatga acatcttaaa gaagatctca accttcgctt gaagaaattg     420
actcatgctg ccccctgcat gctgtttatg aaaggaactc ctcaagaacc acgctgtggt     480
ttcagcaagc agatggtgga aattcttcac aaacataata ttcagtttag cagttttgat     540
atcttctcag atgaagaggt tcgacaggga ctcaaagcct attccagttg gcctacctat     600
cctcagctct atgtttctgg agagctcata ggaggacttg atataattaa ggagctagaa     660
gcatctgaag aactagatac aatttgtccc aaagctccca aattagagga aaggctcaaa     720
```

```
gtgctgacaa ataaagcttc tgtgatgctc tttatgaaag gaaacaaaca ggaagcaaaa      780
tgtggattca gcaaacaaat tctggaaata ctaaatagta ctggtgttga atatgaaaca      840
ttcgatatat tggaggatga agaagttcgg caaggattaa aagcttactc aaattggcca      900
acataccctc agctgtatgt gaaaggggag ctggtgggag gattggatat tgtgaaggaa      960
ctgaaagaaa atggtgaatt gctgcctata ctgagaggag aaaatcgc                  1008

<210> SEQ ID NO 2
<211> LENGTH: 25
<212> TYPE: RNA
<213> ORGANISM: Homo sapiens

<400> SEQUENCE: 2
ugagggaguu cuuuagcuaa cucug                                            25

<210> SEQ ID NO 3
<211> LENGTH: 25
<212> TYPE: RNA
<213> ORGANISM: Homo sapiens

<400> SEQUENCE: 3
cagaguuagc uaaagaacuc ccuca                                            25

<210> SEQ ID NO 4
<211> LENGTH: 21
<212> TYPE: DNA
<213> ORGANISM: Homo sapiens

<400> SEQUENCE: 4
gtggaaattc ttcacaaaca t                                                21
```